United States Patent
Kanitz et al.

(10) Patent No.: US 7,858,724 B2
(45) Date of Patent: Dec. 28, 2010

(54) POLYMERIC, PHOSPHORESCENT, ORGANICALLY SEMI-CONDUCTIVE EMITTER MATERIALS BASED ON PERARYLATED BORANES, METHOD FOR THEIR PRODUCTION AND USE THEREOF

(75) Inventors: Andreas Kanitz, Hoechstadt (DE); Wolfgang Rogler, Moehrendorf (DE); Wolfgang Roth, Uttenreuth (DE); Thomas Sonnabend, Bernburg (DE); Jasmin Woerle, Fuerth (DE)

(73) Assignee: Osram Opto Semiconductors GmbH, Regensburg (DE)

( * ) Notice: Subject to any disclaimer, the term of this patent is extended or adjusted under 35 U.S.C. 154(b) by 0 days.

(21) Appl. No.: 10/585,182

(22) PCT Filed: Dec. 29, 2004

(86) PCT No.: PCT/DE2004/002833

§ 371 (c)(1), (2), (4) Date: Mar. 29, 2007

(87) PCT Pub. No.: WO2005/063919

PCT Pub. Date: Jul. 14, 2005

(65) Prior Publication Data

US 2007/0191587 A1    Aug. 16, 2007

(30) Foreign Application Priority Data

Dec. 29, 2003   (DE)   ................ 103 61 385

(51) Int. Cl.
  C08G 79/08   (2006.01)
  C08G 79/00   (2006.01)
(52) U.S. Cl. ................ 528/4; 528/9; 528/394
(58) Field of Classification Search ........ 528/394, 528/4, 9
See application file for complete search history.

(56) References Cited

U.S. PATENT DOCUMENTS

| | | | |
|---|---|---|---|
| 3,100,181 A * | 8/1963 | Ryznar et al. ............ 205/420 |
| 3,213,136 A | 10/1965 | Washburn et al. | |
| 3,311,662 A * | 3/1967 | Washburn et al. .......... 568/3 |
| 4,239,738 A * | 12/1980 | Richardson ............ 423/292 |
| 5,681,870 A | 10/1997 | Keller et al. | |
| 5,807,905 A * | 9/1998 | Cunningham et al. ....... 522/25 |
| 6,025,454 A * | 2/2000 | Sneddon et al. ............. 528/7 |
| 6,057,078 A * | 5/2000 | Cunningham et al. ..... 430/269 |
| 6,248,265 B1 * | 6/2001 | Lee et al. ............ 260/665 G |
| 6,960,364 B2 * | 11/2005 | Suzuri et al. ............. 427/66 |
| 6,984,459 B1 * | 1/2006 | Noguchi et al. .......... 428/690 |
| 7,033,680 B2 * | 4/2006 | Tanaka et al. ............ 428/690 |
| 7,041,910 B2 * | 5/2006 | Swager et al. ......... 174/110 R |
| 7,060,369 B2 * | 6/2006 | Stossel et al. ........... 428/690 |
| 7,125,998 B2 * | 10/2006 | Stossel et al. ............ 546/4 |
| 7,239,766 B2 * | 7/2007 | Mechery et al. ........... 385/12 |
| 7,311,982 B2 * | 12/2007 | Christou et al. .......... 428/690 |
| 7,323,533 B2 * | 1/2008 | Becker et al. ............. 528/86 |
| 2002/0034656 A1 * | 3/2002 | Thompson et al. ........ 428/690 |
| 2003/0006411 A1 | 1/2003 | Kido et al. | |
| 2003/0091862 A1 * | 5/2003 | Tokito et al. ............ 428/690 |
| 2003/0143429 A1 * | 7/2003 | Suzuki et al. ........... 428/690 |
| 2003/0186080 A1 * | 10/2003 | Kamatani et al. ......... 428/690 |
| 2004/0002576 A1 * | 1/2004 | Oguma et al. ............. 528/4 |
| 2004/0028943 A1 * | 2/2004 | Hartmann et al. ........ 428/690 |
| 2004/0059124 A1 * | 3/2004 | Cyr et al. ............. 548/263.2 |
| 2004/0195965 A1 * | 10/2004 | Yamazaki et al. .......... 313/506 |
| 2004/0202892 A1 * | 10/2004 | Yasuda et al. ........... 428/690 |
| 2004/0247934 A1 * | 12/2004 | Takeuchi et al. ......... 428/690 |
| 2005/0123794 A1 * | 6/2005 | Deaton et al. ........... 428/690 |
| 2005/0147843 A1 * | 7/2005 | Kobayashi et al. ........ 428/690 |
| 2005/0177002 A1 * | 8/2005 | Yamamoto et al. ......... 564/10 |
| 2005/0186443 A1 * | 8/2005 | Marrocco et al. ......... 428/690 |
| 2005/0227108 A1 * | 10/2005 | Lewis et al. ............ 428/690 |
| 2006/0063026 A1 * | 3/2006 | Holmes et al. ........... 428/690 |
| 2006/0093852 A1 * | 5/2006 | Marsitzky et al. ........ 428/690 |
| 2006/0134461 A1 * | 6/2006 | Huo et al. .............. 428/690 |
| 2006/0222758 A1 * | 10/2006 | Taka et al. ............... 427/66 |
| 2006/0229431 A1 * | 10/2006 | Kanitz et al. ............ 528/394 |
| 2007/0155928 A1 * | 7/2007 | Koyama et al. .......... 526/310 |

FOREIGN PATENT DOCUMENTS

| | | |
|---|---|---|
| CN | 1160058 | 9/1997 |
| CN | 1434060 A | 8/2003 |
| DE | 10 2004 001 865 A1 | 12/2004 |
| DE | 103 37 077 A1 | 3/2005 |
| EP | 0 775 706 B1 | 5/1997 |
| EP | 1 142 895 A1 | 10/2001 |
| EP | 1 385 919 B1 | 2/2004 |
| JP | 2000-294373 | 10/2000 |
| JP | 2003-031368 | 1/2003 |
| WO | WO 02/12212 A1 | 2/2002 |

(Continued)

OTHER PUBLICATIONS

Motoi Kinoshita et al., "A Novel Family of Boron-Containing Hole-Blocking Amorphous Molecular Materials for Blue- and Blue-Violet-Emitting Organic Electroluminescent Devices", Dec. 2002, Advanced Functional Materials, 12, No. 11-12, pp. 780-786.

International Search Report and Written Opinion, International Application Serial No. PCT/DE2004/002833, May 19, 2005, 7 pp.

(Continued)

*Primary Examiner*—Mark Eashoo
*Assistant Examiner*—Liam J Heincer
(74) *Attorney, Agent, or Firm*—Fish & Richardson P.C.

(57) ABSTRACT

The invention relates to luminescent compounds with semi-conducting properties, as well as their production and their use in organic light-emitting diodes (OLEDs). The compounds are copolymers comprising a metal complex with a central atom from subgroup 8 of the periodic table of elements.

13 Claims, 2 Drawing Sheets

FOREIGN PATENT DOCUMENTS

| WO | WO 02/071813 A1 | 9/2002 |
| --- | --- | --- |
| WO | WO 02/074015 A2 | 9/2002 |
| WO | WO 03/018712 A1 | 3/2003 |
| WO | WO 03/091355 A2 | 11/2003 |
| WO | WO 03091355 A2 * | 11/2003 |
| WO | WO 2004099291 A1 * | 11/2004 |

OTHER PUBLICATIONS

English Translation of International Preliminary Report on Patentability and Written Opinion of the International Search Authority, International Application Serial No. PCT/DE2004/002833, Aug. 29, 2006, 5 pp.

Chihaya Adachi et al., "Endothermic energy transfer: A mechanism for generating very efficient high-energy phosphorescent emission in organic materials", Applied Physics Letters, Sep. 24, 2001, vol. 79, Issue 13, pp. 2082-2084.

Sergey Lamansky et al., "Highly Phosphorescent Bis-Cyclometalated Iridium Complexes: Synthesis, Photophysical Characterization, and Use in Organic Light Emitting Diodes", 2001, Journal American Chemical Society, vol. 123, No., pp. 4304-4312.

Sergey Lamansky et al, "Synthesis and Characterization of Phosphorescent Cyclometalated Iridium Complexes", 2001, Inorganic Chemistry, vol. 40, No. 7, pp. 1704-1711.

Noriyoshi Matsumi et al., "Poly(p-phenlene-borane)s. Novel Organoboron π-Conjugated Polymers via Grignard Reagent", J. Am. Chem. Soc., 1998, 120, pp. 10776-10777.

Hidekaru Doi et al., "A Novel Class of Emitting Amorphous Molecular Materials with Bipolar Character for Electroluminescence", 2003, Chem. Mater., vol. 15, No. 5, pp. 1080-1089.

Gompper et al., Synthesis of Oligo(diazaphenyls). Tailor-Made Fluorescent Heteroaromatics and Pathways to Nanostructures, Feature Article, (1997), pp. 696-708.

* cited by examiner

POLYMERIC, PHOSPHORESCENT, ORGANICALLY SEMI-CONDUCTIVE EMITTER MATERIALS BASED ON PERARYLATED BORANES, METHOD FOR THEIR PRODUCTION AND USE THEREOF

BACKGROUND

The invention relates to luminophorous compounds with semi-conducting properties as well as their production and their use in organic light-emitting diodes (OLEDs).

So-called "small molecules" (i.e. individual molecules featuring luminophorous properties for OLED applications) with perarylated borane structures are known in the art, for example, from the publication by M. Kinoshita et al., "Boron containing Materials for blue/blue-violet Electroluminescence."

Also known are luminophores that phosphoresce, in particular for small molecule OLED applications; see, for example, publications and patents by M. E. Thompson and S. R. Forrest.

The disadvantage of small molecules lies in the fact that they are difficult to apply because individual molecules cannot be produced as OLED layers by way of spin coating or other coating methods; instead in this context expensive application methods are needed.

SUMMARY

It is therefore the object of the present invention to provide new organic, polymeric, semi-conducting emitter and transport materials that can be used in organic light-emitting diodes and/or light-emitting diode displays, that are, in terms of preparation, easily accessible and that can be easily processed by mass production.

DETAILED DESCRIPTION

Figure 1:
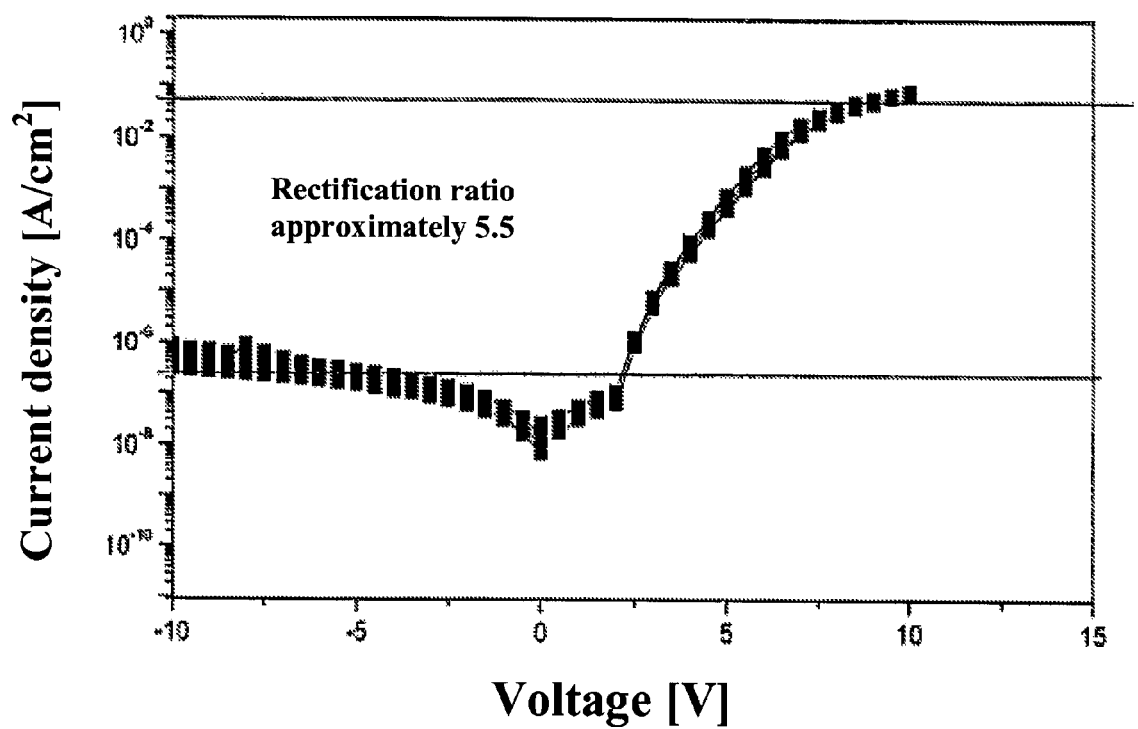
FIG. 1 is a graph of current density as a function of voltage for an embodiment of an OLED.

The subject-matter of the present invention includes phosphorescing co-polyaryl boranes of type K,

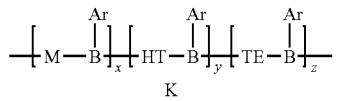

K wherein the following applies:

x, y and z are molar parts of components and add up to 1, and the part z has a value of between 0.01 and 0.1, and the ratios of parts x and y are freely selectable in the range of the difference relative to 1;

hydrogen atoms are bonded at the ends;

M, HT and TE stand for the type of the respective arylene component in the copolymer;

and M serves hereby as a matrix structure comprising an arylene structure, preferably the 2,7-fluoroenylene structure which can also be easily substituted in the 9-position with linear and/or branched alkyl moieties (C1 to C10); and the term arylene structure denotes any bivalently linking single- or multi-nucleic aromatic and/or heteroaromatic structure, such as indicated, for example, in table 1 (a-x)

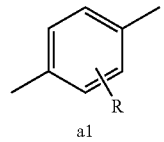

a1

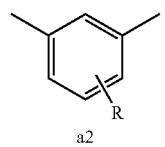

a2

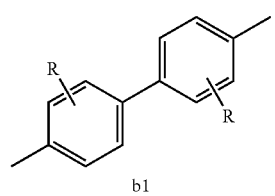

b1

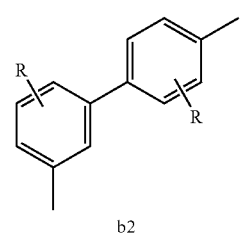

b2

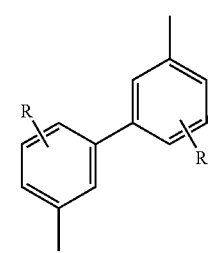

b3

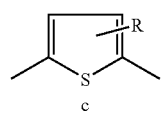

c

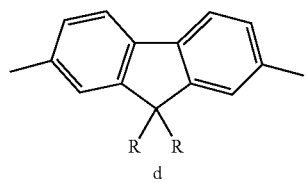

d

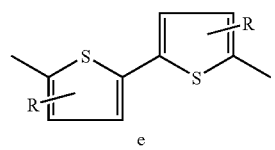

e

-continued
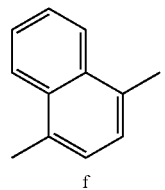
f
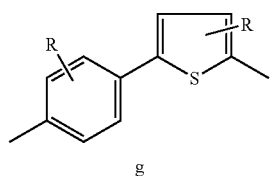
g
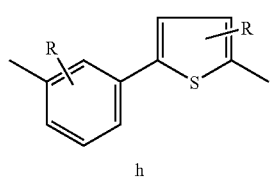
h
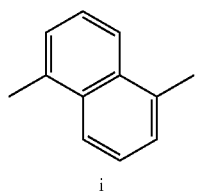
i
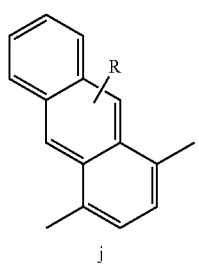
j
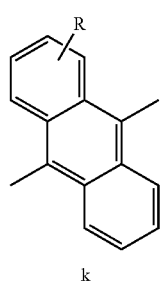
k
-continued
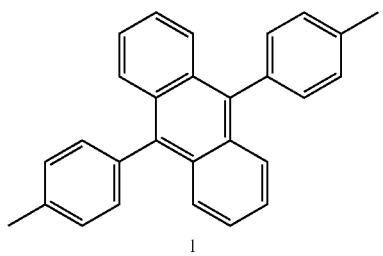
l
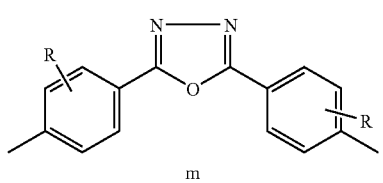
m
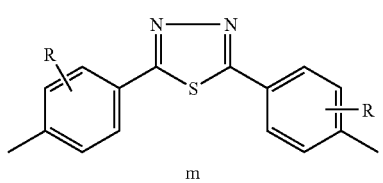
m
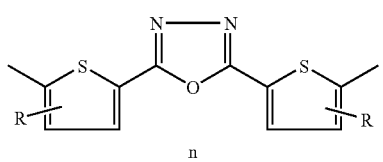
n
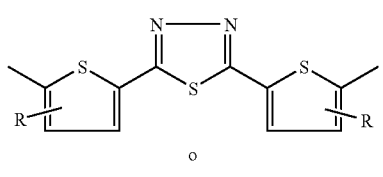
o
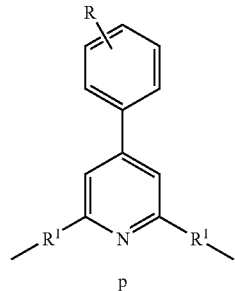
p -continued

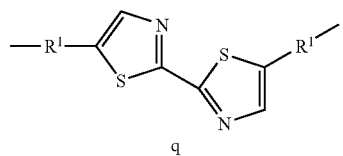
q

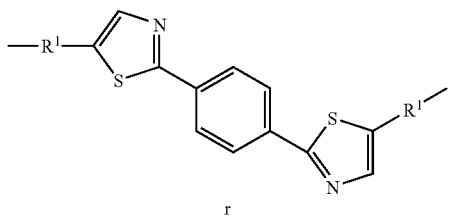
r

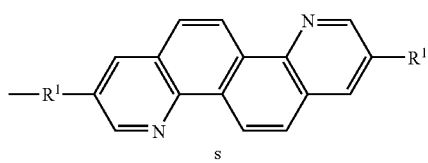
s

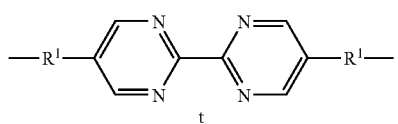
t

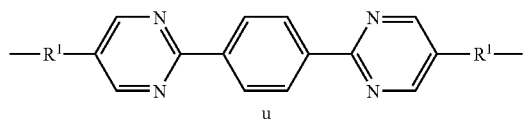
u

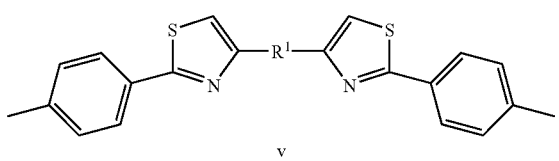
v

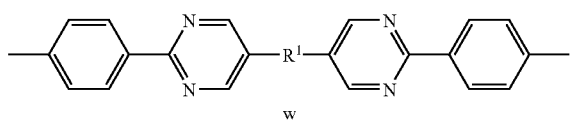
w

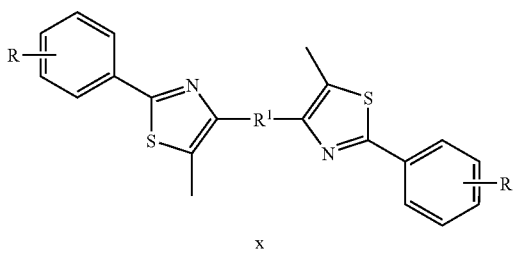
x the solubility of which in organic solvents can be further improved by any additional arrangement of one or several linear and/or branched alkyl substituents, plus or alternatively, alkoxy substituents R, or also by way of alkyl-substituted arylene substituents $R^1$; and used preferably for this purpose are 2,7-disubstituted 9,9-dialkyl-fluoroenylene structures equipped with branched or linear alkyl groups of C5 to C10 that are easy to synthesize.

HT is a substituted 2-amino-thiophene and/or -thiazole structure with hole-transport capability comprising various possibilities as follows in that:

HT(a) can be a substituted (2,2'diamino-5,5'bisthienyl)-4,4'-ylene structure,

HT(b) can be a substituted bis-N,N'-(thien-2-yl)- and/or bis-N,N'-(1,3-thiazol-2-yl)-diaminoarylene structure, and HT(c) can be a substituted (2,2'-diamino)-bis-(4,4'thienyl)-arylene-5,5'-ylene structure, respectively in accordance with the formulas shown below, and the substituents $R^2$, $R^3$ and $R^4$ represent aryl groups Ar that in turn can be substituted by any additional arrangement of one or several linear and/or branched alkyl substituents, plus or alternatively, alkoxy substituents R, and in this context the denotations of substituents R″ with same index n are identical and those of substituent $R^1$ are identical with the substituent selection for arylene component Md;

In addition in this context it applies for HT(b) that X is equal to N or C-R. The HT component serves to achieve optimal adjustment of the hole transport properties and for longer-wave emission correction of the copolymer

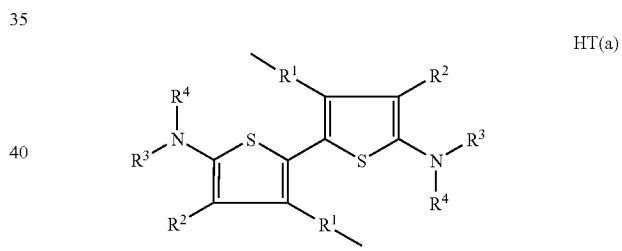
HT(a)

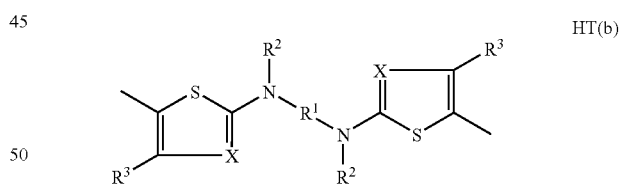
HT(b)

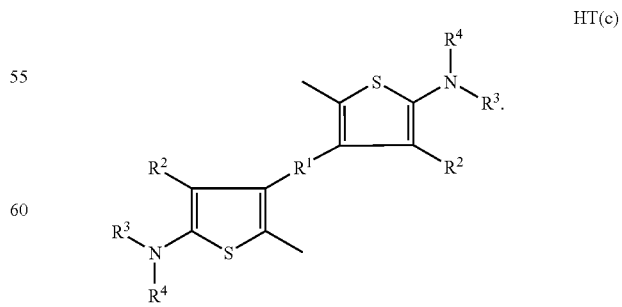
HT(c)

TE is a bivalent, phosphorescing organo-metallic complex of the following structure:

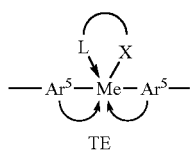

TE

Me denotes a metal of subgroup 8 (iridium, ruthenium, osmium or platinum); iridium is preferred.

$Ar^5$ is an arylene ligand that can form a complex with the metal which carries, simultaneously, a function for polymeric linking, the ligand (L-X) does not apply for platinum complexes, but for all other metal complexes also included are arylene ligands having the capability of forming complexes such as (a), 1,3-diketonate ligands (b), bis-thiazolylmethane ligands and/or bis-thiazolylamine ligands (c), picolinate ligands (d), N-alkylsalicylaldimino ligands (e) or 8-hydroxyquinolate ligands or (f) preferably of the following structures:

a) Mononuclear complexes:

TE(a)

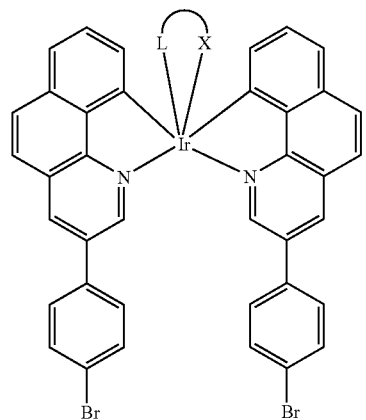

TE(b)

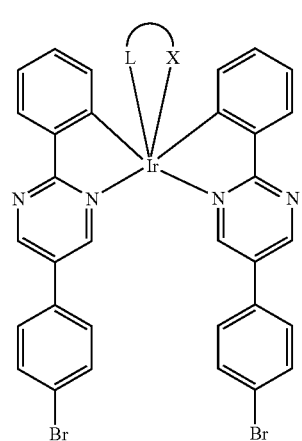

-continued

TE(c)

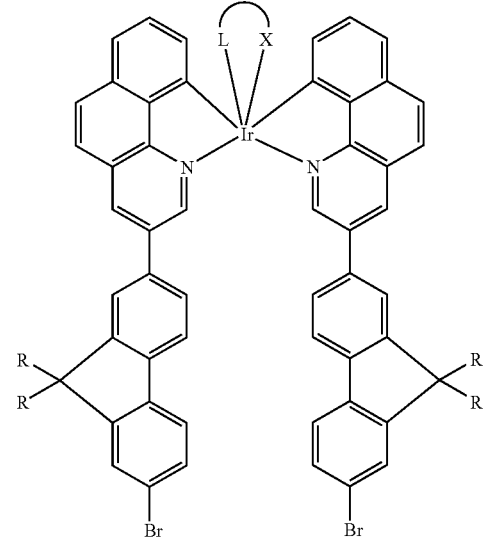

TE(d)

TE(e)

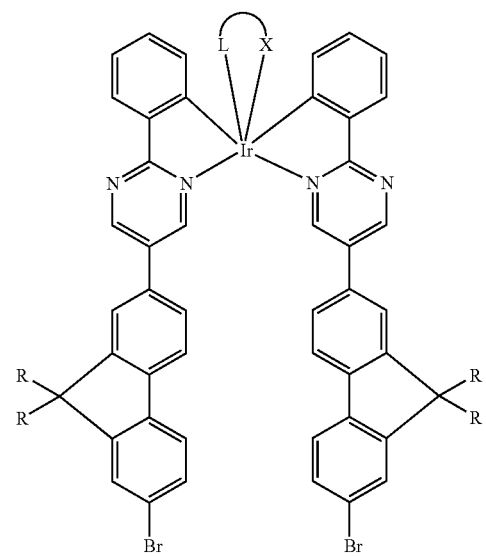

b) Binuclear complexes:
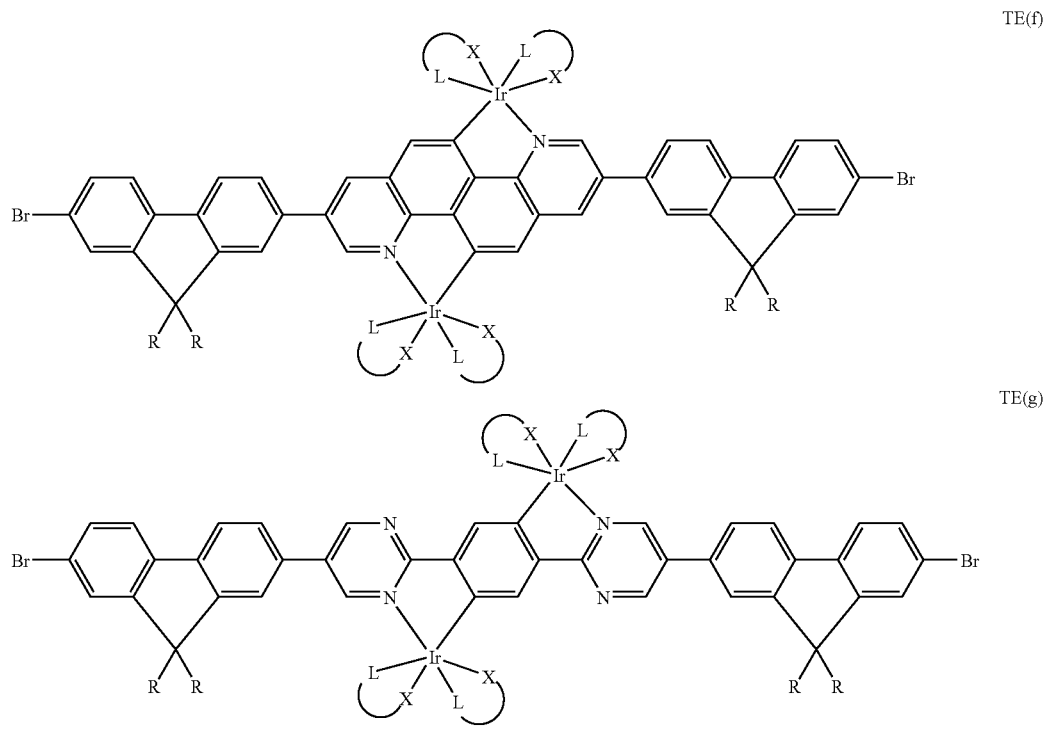
TE(f)
TE(g)
wherein LX ligands are:
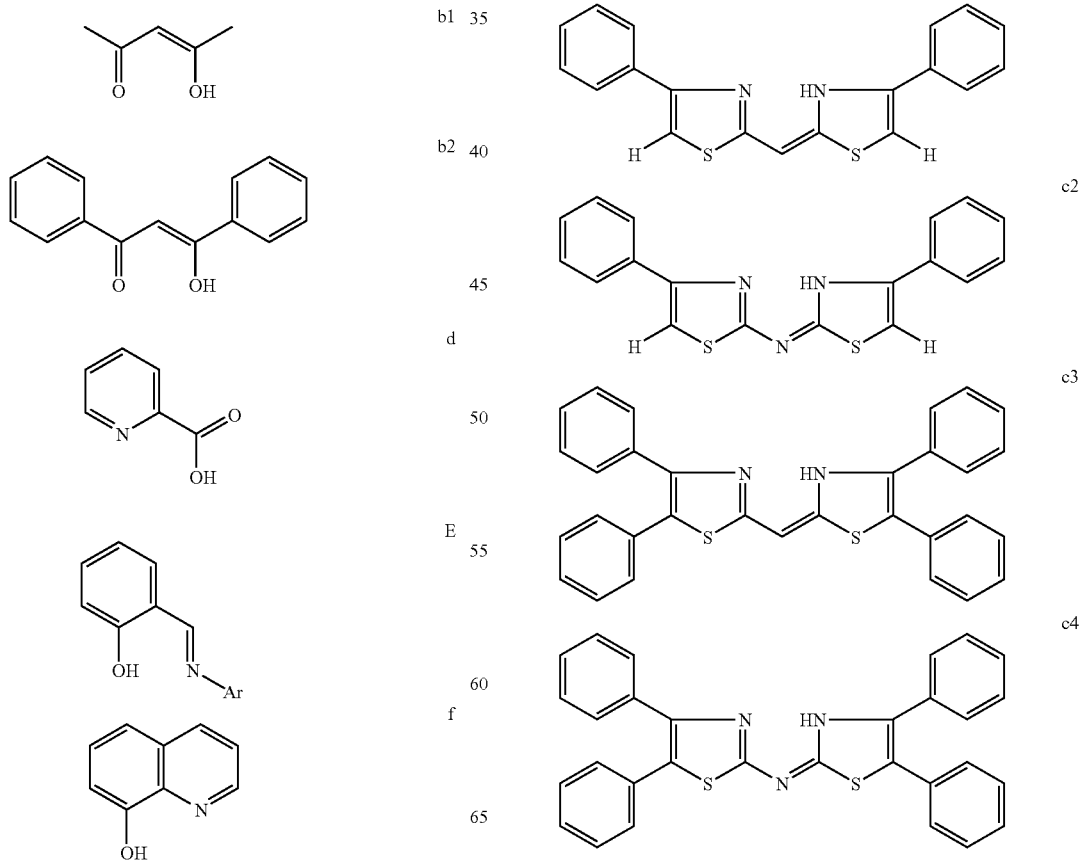

a1
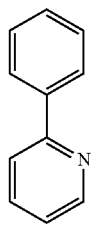

a2
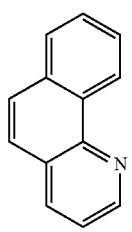

a3
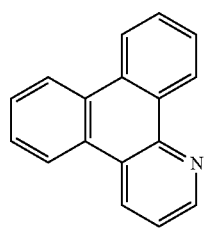

a4
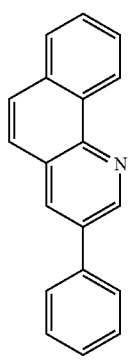

a5
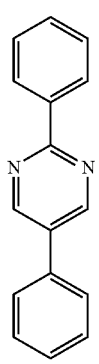

a6
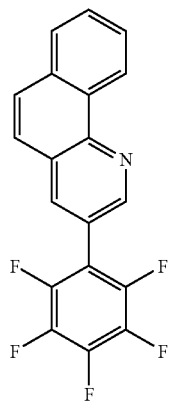

a7
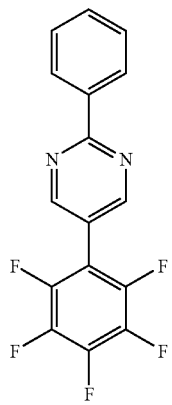

Ar is a carbocyclic or heterocyclic aryl moiety the hydrogen atoms of which can also, if so desired, be substituted by any one or several branched or linear alkyl moieties or alkoxy moieties (C1 to C10) as well as phenyl moieties and/or diphenyl and/or naphthylphenyl amino groups; preferred are mesityl, phenyl, biphenylyl, 1-naphthyl, 2-naphthyl, 2-diphenyl and/or 2-naphthylphenylamino-3,4-diphenyl-thien-5-yl- and 2-diphenyl- and/or 2-naphthylphenylamino-3,4-diphenyl-1,3-thiazol-5-yl.

Furthermore, the subject of the present invention comprises a method for producing the phosphorescing co-polyaryl boranes of type K in accordance with the following general production model:

Reaction scheme:

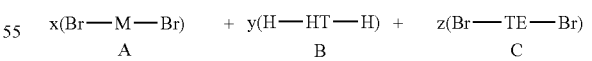

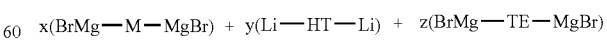

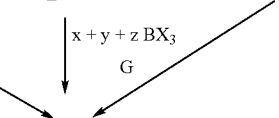

-continued

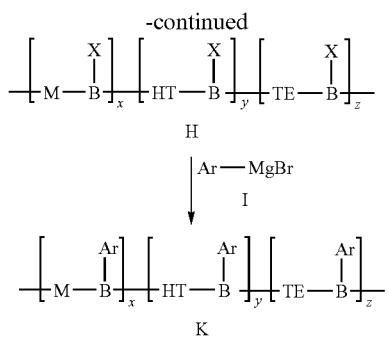

wherein the bromo-substituted arylene components M, hole transport components HT and bromo-substituted phosphorescing organo-metallic complexes TE form the basis; their polarity is reversed by way of a Grignard reaction (as shown in the scheme) or by way of lithiation, and they are subsequently substituted with boron, and for the products H of this reaction the halogens on the boron are substituted once again with organic moieties R, using a Grignard reagent (as shown in the scheme) or a corresponding lithium-based reagent.

Finally, the subject of the present invention comprises the use of the co-polyaryl boranes of type K in organic light-emitting diodes as triplet-emitting species and as an electron-transporting layer.

The subject of the invention is, moreover, also the use of the co-polyaryl boranes K as blends of individual component polymers, which means in the instances in which two of the ratio variables x, y and/or z have the value of zero.

Variables x, y and z are aspect ratios indicating at what ratios the individual polymeric components are co-polymerized relative to each other. The individual polymeric components can also be used, respectively, as material for an electroluminescing layer.

General description of the synthesis path:

On the basis of the starting synthons A, B and C, the Grignard reactions are carried out with magnesium tetrahydrofuran or lithiations with BuLi in ether. The products of the Grignard reactions and/or the organo-lithium reagents D, E and F are reacted, individually or under any desired conditions, with a boron halide G (e.g., boron trifluoride etherate) in THF heated to boiling in such a way that the molar sum of the Grignard components and/or of the organo-lithium compounds corresponds to the molar quantity of the boron halide. In this context, the reaction of the bifunctional Grignard components at approximately 70° C. results in only one linear co-polyfluoroarylene borane H.

Then a further monofunctional Grignard component I is synthesized, and after the solvent THF has been replaced with toluene, (now heating the toluene to boiling) this component is added dropwise at the molecular ratio. After boiling for 5 hours at approximately 120° C., this will lead to the substitution of the remaining fluorine by the aryl moiety of the Grignard component I while forming a phosphorescing co-polyaryl borane derivative K having, based on the component ratios, customized electrical and optical properties.

The phosphorescing polyaryl borane derivatives K are obtained also if, instead of Grignard compound I, the corresponding lithiated component is synthesized, with dry ice cooling, in ether and/or tetrahydrofuran and reacted with the previously synthesized co-polyfluoroarylene borane H.

EMBODIMENTS

Synthesis of Conjugated, Condensed and Oligo Aryl Systems

If the required aryl systems are not commercially available, these systems are obtained by way of known C-C cross-linking reactions (e.g., Suzuki coupling); prior to this, alkylations and/or alkoxylations are effected on at least one coupling component in order to achieve good solubility of the polymeric materials that are to be obtained therefrom.

Synthesis of Dibromo-arylenes M

Obtaining 9,9-diheptyl-2,7-dibromofluorenes

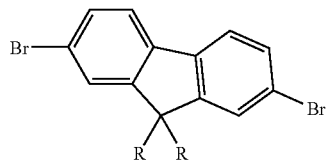

a) Obtaining 9,9-diheptyl-fluorene 0.2 mol fluorene is dissolved in 300 ml DMSO at 80° C. 0.01 mol phase transfer catalyst (aliquot) is added to the solution, and the substance is stirred for another 5 minutes. 0.5 mol 50% caustic soda solution and 0.5 mol heptyl bromide are needed for the alkylation. The addition is effected in three stages, starting with the addition of one third of the overall quantity of caustic soda solution. The solution changes color to deep red and slowly turns yellow after the heptyl bromide has been added. After the solution has turned yellow, the second third of caustic soda solution is added, etc. The end of the reaction is controlled by way of DC on RP18 in acetonitrile.

The reaction mixture is extracted three times with ether and water, and the organic phase is separated. After all solvents (ether, DMSO, heptanol) have been distilled off, the product remains in the form of a yellow oil (HPLC control). It is then further processed as a raw product. Alkyl bromides R-Br (R is e.g., decyl- or a 2-ethylhexyl group) are used in order to obtain corresponding 9,9-dialkylfluorenes with alkyl groups other than the heptyl group.

b) Obtaining 2,7-dibromo-9,9-diheptylfluorene 0.2 mol diheptylfluorene is dissolved in 300 ml chloroform and heated to a boil. 0.4 mol bromine, dissolved in chloroform, is slowly added dropwise in the dark. The reaction is stirred for approximately 12 hours at boiling heat. When the reaction solution has become decolorized, the bromination is complete (DC control on RP18 in acetonitrile). After the solution has cooled down, the entirety of the chloroform is distilled off and the product is precipitated in methanol as white crystals. Following chromatography on silica gel in cyclohexane an HPLC-pure product is obtained with mp: 45-46° C.

Synthesis of Dibromo-arylene HT/Make-up of the Structures HT(a)

1. Dialkylation of 2-bromofluorene 0.1 mol 2-bromofluorene is dissolved in DMSO under a nitrogen atmosphere, while stirring continuously at approximately 50° C. The dissolved 2-bromofluorene is mixed with 0.25 mol potassium-tert.-butyl oxide causing the reaction mixture to turn dark red. After 5 minutes, 0.25 mol alkyl bromide R-Br is added; the reaction runs its course overnight at room temperature and is complete when a color change from red to light-yellow occurs.

The DMSO phase is washed with water and extracted using ether. The ether is distilled off with a rotary evaporator, and the product is precipitated in methanol in the form of light-yellow crystals.

1a) 2-bromo-9,9-diheptylfluorene

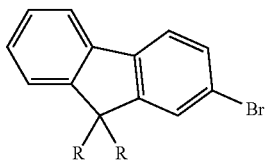

2-bromo-9,9-diheptylfluorene (mp: 32° C.) is synthesized in this manner, for example, from 2-bromofluorene and heptylbromide in the presence of potassium-tert.-butyl oxide.

2. Chloroacetylation of 9,9-dialkyl-2-bromofluorenes 0.1 mol 9,9-diheptyl-2-bromofluorene is prepared in methylene chloride and cooled down to −15° C. with liquid nitrogen. When a temperature of −15° C. is reached, 0.15 mol chloroacetylchloride is added, then 0.3 mol aluminum chloride. The reaction is then stirred overnight (at least for 12 hours).

The mixture is poured in ice/water/HCl (500 ml: 500 ml: 50 ml) and stirred for 20 minutes. Afterwards another washing with water is performed. The organic phase is separated and the solvent distilled off. The product is precipitated in methanol in the form of white crystals.

2a) 2-bromo-7-chloroacetyl-9,9-diheptylfluorene

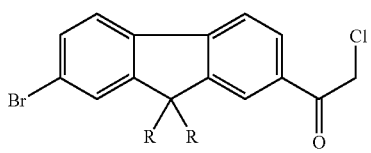

2-bromo-7-chloroacetyl-9,9-diheptylfluorene (mp: 83-84° C.) is produced in this manner, for example, from 2-bromo-9,9-diheptylfluorene and chloroacetylchloride under Friedel-Crafts conditions.

3. Synthesis of arylated carboxamides 1 mol of a secondary diarylamine is dissolved in 600 ml dioxane using a 2l three-necked flask with reflux cooler, magnetic agitator, tap funnel and inert gas flow-through. The required carboxylic acid halide is then added dropwise in an equivalent quantity. Subsequently, the reaction mixture is heated with reflux until the total quantity of the hydrohalogenide that is generated during the reaction has been removed from the inert gas flow. Thin layer chromatography is used to assist in detecting the end of the reaction. The reaction solution is then cooled down and stirred into at least double the quantity of water. In most cases this will lead to the separation of an oil which has become solidified after some hours. The aqueous phase is separated and the raw product is recrystallized from ethanol. The yield is typically at least 90%.

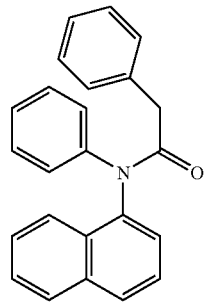

3a) 2-phenyl-acetic acid-phenyl-1-naphthylamide (mp: 85-88° C.) is produced in this manner, for example, from phenyl-1-naphthyl-amine and 2-phenylacetyl chloride

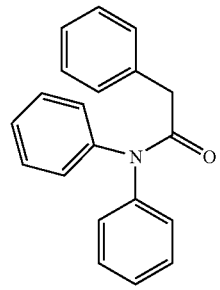

3b) 2-phenyl-acetic acid-diphenylamide (mp: 71-72° C.) is produced in this manner, for example, from diphenylamine and 2-phenylacetyl chloride 4. Synthesis of arylated thiocarboxamides 0.5 mol of the particular arylated carboxamide and the equivalent quantity Lawesson's reagent (made of anisole and phosphorous pentasulfide) are suspended in a reflux apparatus with inert gas flow-through in 750 ml diglycoldiethylether; subsequently, the substance is stirred for 6 hours at 100° C. Resulting from this is a clear solution from which, when chilled, the reaction product becomes crystallized in some cases. To isolate the product completely, the reaction mixture is stirred in with double the amount of water; the oily phase that often forms can then be crystallized. Afterwards the product is separated from the aqueous phase and recrystallized from methanol. The yield is typically at least 90%.

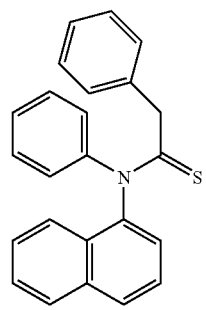

4a) 2-phenylthio-acetic acid-phenyl-1-naphthalamide (mp: 100-103° C.) is produced in this manner, for example, from 2-phenyl-acetic acid-phenyl-1-naphthylamide and Lawesson's reagent

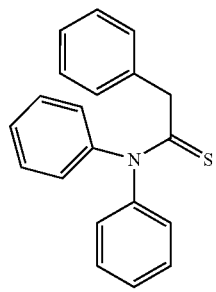

4b) 2-phenylthio-acetic acid-diphenylamide (mp: 142-144° C.) is produced in this manner, for example, from 2-phenyl-acetic acid-diphenylamide and Lawesson's reagent 5. Obtaining arylated 2-aminothiophene derivatives 0.1 mol haloacylaryl derivative is prepared with 0.1 mol 2-phenylthio-acetic acid-diarylamide (example 4b) in tetrahydrofuran and refluxed for 30 minutes in a nitrogen atmosphere. 0.1 mol trimethylamine is added after 30 minutes, and the mixture is refluxed for another 30 minutes. The product is precipitated in methanol in the form of yellowish crystals.

5a) 2-(phenyl-1-naphthylamino)-3-phenyl-4-p-bromophenyl-thiophene

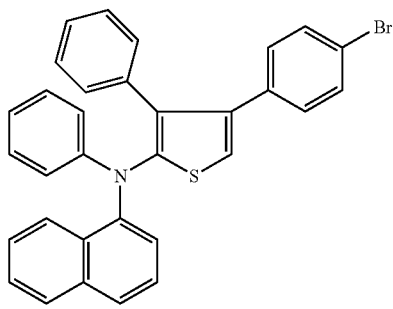

2-(phenyl-1-naphthylamino)-3-phenyl-4-p-bromophenylthiophene (ESI-MS: M+1⁺=532) is produced in this manner, for example, from 2-phenylthio-acetic acid-phenyl-1-naphthylamide and p-bromophenacyl bromide.

5b) 2-(phenyl-1-naphthylamino)-3-phenyl-4-(7-bromo-9,9-diheptyl-fluoren-2-yl)-thiophene

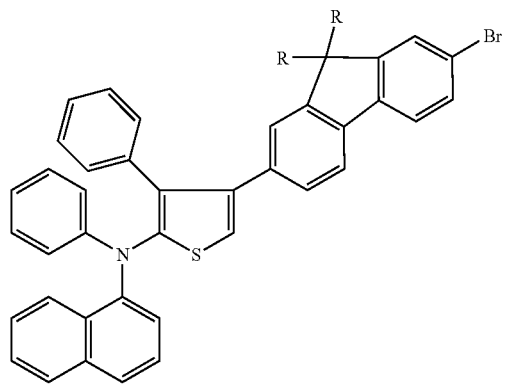

2-(phenyl-1-naphthylamino)-3-phenyl-4-(7-bromo-9,9-diheptyl-fluoren-2-yl)-thiophene is produced in this manner, for example, with R=heptyl (ESI-MS: M+1⁺=816) from 2-phenylthio-acetic acid-phenyl-1-naphthylamide and 2-chloroacetyl-7-bromo-9,9-diheptyl-fluorene.

6. Obtaining dibromo-arylene derivatives with hole transport properties via oxidation of 2-aminothiophene derivatives A 0.1 mol 2-aminothiophene derivative is combined with 0.5 mol FeCl₃ in methylene chloride, and the mixture is stirred for one day. The product is mixed with water and 0.1 mol triethylamine, and the organic solvent is distilled off. The product is now precipitated in the remaining aqueous phase in the form of yellow crystals. The crystals are cleaned via column chromatography (on silica gel with toluene).

6a) Bis-[2-(phenyl-1-naphthylamino)-3-phenyl-4-(7-bromo-9,9-diheptyl-fluoren-2-yl)]-5,5'-thienyl

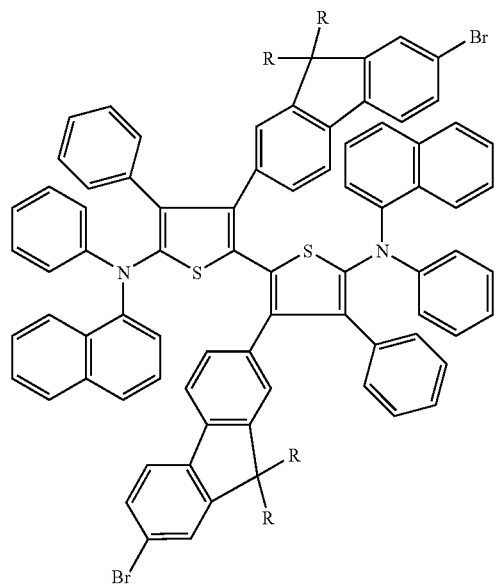

Bis-[2-(phenyl-1-naphthylamino)-3-phenyl-4-(7-bromo-9,9-dialkyl-fluoren-2-yl)]-5,5'-thienyl with R=heptyl (ESI-MS: M+1⁺=1629) is produced in this manner, for example, from 2-(phenyl-1-naphthylamino)-3-phenyl-4-(7-bromo-9,9-diheptyl-fluoren-2yl)-thiophene and iron-III chloride.

6b) Bis-[2-phenyl-1-naphthylamino)-3-phenyl-4-(4-bromophenyl)]-5,5'-thienyl

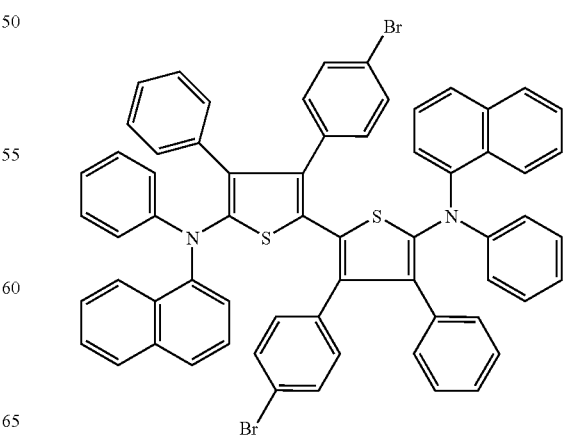

Bis[2-phenyl-1-naphthylamino)-3-phenyl-4-(4-bromophenyl)]-5,5'-thienyl (mp: 133-134° C.), (ESI-MS: M+1+= 1061) is produced in this manner, for example, from 2-(phenyl-1-naphthylamino)-3-phenyl-4-(4-bromophenyl)-thiophene and iron-III chloride.

Synthesis of Dibromo-arylene HT/Makeup of the Structures HT (b)

1. Synthesis of arylated biscarboxamides 1 mol of a respective secondary arylated bisamine is dissolved in 600 ml dioxane using a 2 l three-necked flask with reflux cooler, magnetic agitator, tap funnel and inert gas flow-through. The required equivalent quantity of the respective carboxylic acid halide is then dropped in. Subsequently, the mixture is heated with reflux until the total quantity of the hydrohalogenide resulting from the reaction has been removed from the inert gas flow. Thin layer chromatography can additionally be used to detect the end of the reaction. The reaction solution is then cooled down and stirred in with at least twice the amount of water. In most cases an oil becomes separated during this process and becomes solidified after a few hours. The aqueous phase is separated and the raw product is recrystallized from ethanol. The yield is typically at least 90%.

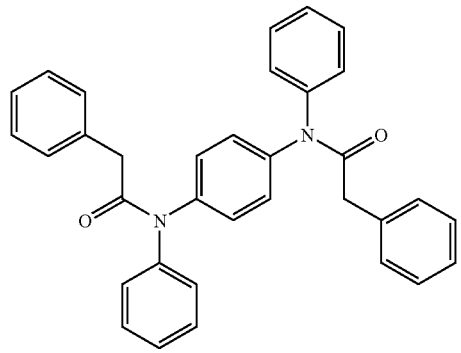

1a) N,N'-di(2-phenylacetyl)-N,N'-diphenyl-phenylene-1,4-diamine (mp: 190° C.) is produced in this manner, for example, from N,N'-diphenyl-p-phenylene diamine and 2-phenylacetyl chloride.

2. Synthesis of arylated bisthiocarboxamides 0.5 mol of the respective arylated biscarboxamide and the equivalent quantity of Lawesson's reagent (synthesized of anisole and phosphorous pentasulfide) are suspended in a reflux apparatus with inert gas flow-through in 750 ml diglycoldiethyl ether; then the mixture is stirred for 6 hours at 100° C. This leads to a clear solution from which, when chilled, in some cases the reaction product becomes crystallized. To isolate the product completely, the reaction mixture is stirred in with double the quantity of water. Frequently, an oily phase forms which is allowed to crystallize. Subsequently, the product is separated from the aqueous phase and recrystallized from methanol. The yield is typically at least 90%.

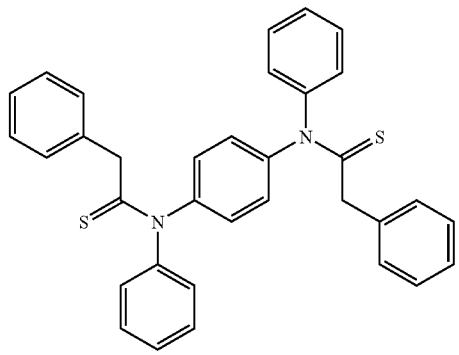

2a) N,N'-di(2-phenylthioacetyl)-N,N'-diphenylen-phenylene-1,4-diamine (mp: 224-227° C.) is produced in this manner, for example, from N,N'-di(2-phenylacetyl)-N,N'-diphenyl-phenylene-1,4-diamine and Lawesson's reagent 3. Obtaining arylated bis-2-aminothiophene derivatives 0.2 mol haloacylaryl derivative is mixed with 0.1 mol N,N'-di(2-phenylthio-acetyl)-N,N'-diphenyl-phenylene-1,4-diamine in tetrahydrofuran and refluxed for 30 minutes in a nitrogen atmosphere. 0.2 mol trimethylamine is added after 30 minutes, and the substance is refluxed for another 30 minutes. The product is precipitated from methanol in the form of light-yellow crystals.

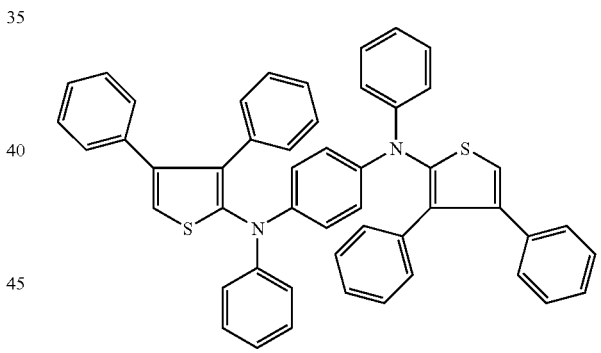

3a) N,N'-diphenyl-N,N'-dithien-3,4-diphenyl-2-yl-phenylene-1,4-diamine (mp: 266-268° C.) is produced in this manner, for example, from N,N'-di(2-phenylthio-acetyl)-N,N'-diphenyl-phenylene-1,4-diamine and phenacyl bromide Synthesis of Dibromo-arylenes HT/Makeup of the Structures HT(c)

1. Obtaining 2,2'-diamino-4,4'-bisthienyl-arylenes 0.1 mol bis-(haloacyl)-arylene derivative is provided with 0.2 mol 2-arylthio-acetic acid-diarylamide in tetrahyrofuran and refluxed for 30 minutes in a nitrogen atmosphere. 0.2 mol trimethylamine is added after 30 minutes, and the substance is refluxed for another 30 minutes. The product is precipitated from methanol in the form of colorless crystals.

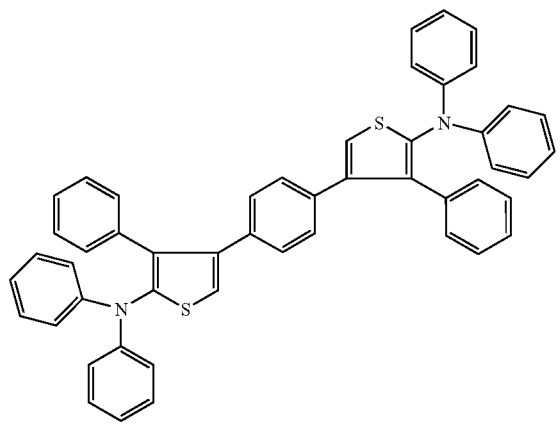

a) 2,2'-diphenylamino-3,3'-diphenyl-4,4'-bisthienyl-p-phenylene (mp: 232-235° C.) is produced in this manner, for example, from 2-phenyl-thioacetic acid-diphenylamide and bis-ω-bromoacetyl-p-phenylene.

Synthesis of Dibromo-arylene Triplet Emitter Complex TE a) Synthesis of the ligands:

a1) Obtaining 2-(4-bromophenyl)-N,N,N',N'-tetramethyl-vinamidinium-perchlorate:

0.1 mol 4-bromophenyl-acetic acid is heated for 3 hours at 80° C. with freshly prepared Vilsmeyer complex (DMF/POCl3). After the DMF has been distilled off in a vacuum, the reaction mixture is added to a cold aqueous solution containing 0.1 mol sodium perchlorate. The precipitated salt is drawn off and washed with some ethanol and ether and suctioned dry. White crystals, mp: 145-147° C.

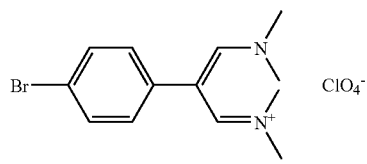

a2) Obtaining 3-(4-bromophenyl)-h-benzoquinoline 0.05 mol vinamidinium salt (a1) is heated with 0.55 mol 1-naphthylamine in DMF with reflux; after 4 to 5 hours the substance is allowed to cool down and the precipitated crystal slush is drawn off, then washed with ethanol and ether. White fluorescent crystals; mp: 160° C.

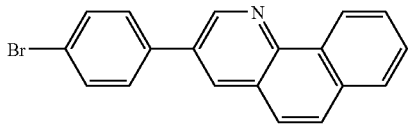

a3) Obtaining 5-(4-bromophenyl)-2-phenylpyrimidine 0.05 mol vinamidinium salt a1 is heated together with 0.055 mol benzamidine hydrochloride in pyridine with reflux; after 12 hours the substance is allowed to cool down, the pyridine is distilled off and methanol is blended in with the reaction mixture. The precipitated crystals are drawn off, then washed with ethanol and ether. White fluorescent crystals; mp: 194° C.

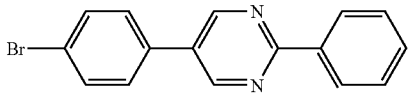

a4) Obtaining 3-(4-bromophenyl)-f,h-dibenzoquinoline 0.05 mol vinamidinium salt 1 is heated together with 0.055 mol 9-aminophenanthrene in DMF with reflux; after 4 to 5 hours the substance is allowed to cool down, the precipitated crystal slush is drawn off and finally washed with ethanol and ether. Fluorescent crystals; mp: ° C.

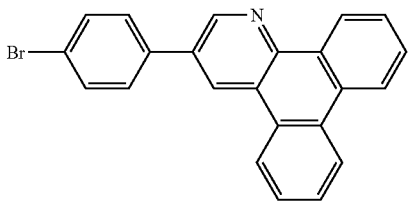

b) Synthesis of the complexes:

1) General instruction for the synthesis of Ir-di-μ-chloro complexes:

0.01 mol iridium chloride is heated together with 2.1 equivalents of an element of 2-phenyl-pyridine-structure (e.g., the ligands a2, a3) in 100 ml methoxyethanol and 25 ml water with reflux. After 12 hours, following cool-down, a yellow product is drawn off and washed with methanol/ether.

1a) A complex of the type $(C\char`\^N)_2$-Ir-μCl$_2$-Ir=$(C\char`\^N)_2$ is formed in this manner, for example, with (C^N)=3-(4-bromophenyl)-h-benzoquinoline), yield of 65%. (mp: >300° C., $\lambda_{max}$=462 nm THF, ESI-MS=1783.7).

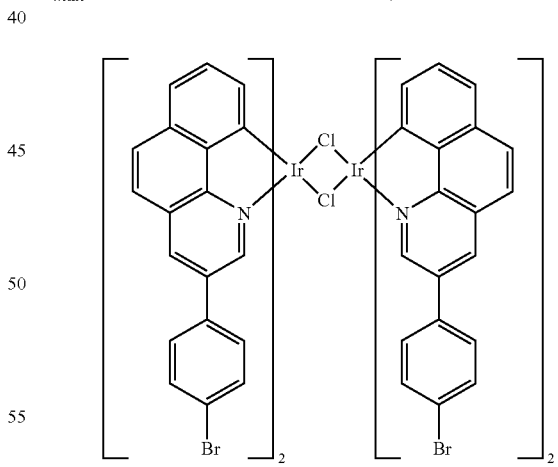

2) General instruction for the synthesis of (C^N)$_2$=Ir-(LX [b-f]) complexes:

0.005 mol Ir-μ-chloro complex is refluxed with 2.1 equivalents of an inorganic LX ligand (b-f) and 0.005 mol sodium carbonate in 30 ml ethoxy ethanol. After 12 hours, the product is stirred-in with five times the amount of methanol, drawn off, washed with methanol/ether and dried.

2a) A complex of the type (C^N)$_2$=Ir-(LX) is formed in this manner, for example, with (C^N)=3-(4-bromophenyl)-h-benzoquinoline and LX=acetyl acetone, yield of 93%. (mp: >300° C., $\lambda_{max\ Emission}$=587 nm THF, ESI-MS=956.1).

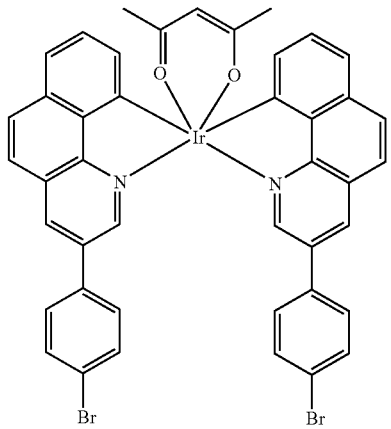

3) General instruction for the synthesis of $(C^\wedge N)_2$=Ir-(LX[a]) complexes:

0.005 mol $(C^\wedge N)_2$=Ir-(acac) complex is refluxed with 1.1 equivalents of an LX ligand of type (a) in 30 ml glycerin. After 12 hours the product is stirred in with five times the quantity of methanol, drawn off, washed with methanol/ether and dried.

3a) A complex of the type $(C^\wedge N)_2$=Ir-(LX) is formed in this manner, for example, with $(C^\wedge N)$=3-(4-bromophenyl)-h-benzoquinoline and LX=phenyl pyridine, yield of 74%. (mp: >300° C., $\lambda_{max\ Emission}$=585 nm, THF, ESI-MS=1011.2).

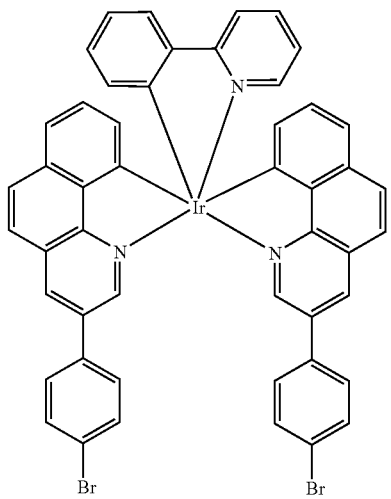

Synthesis of Grignard Compounds D and F 0.25 mol freshly etched magnesium shavings are prepared in an argon atmosphere in dry ether. While stirring and refluxing, 0.1 mol highly purified and dried dibromo-arylene component M (A) or TE (C), dissolved in 300 ml THF, are added dropwise in such a way that the reaction mixture is held at the boiling point following the start of the reaction. The reaction is continued overnight. The synthesis of the required Grignard compounds should, if possible, be conducted in parallel steps so that they are available the next day.

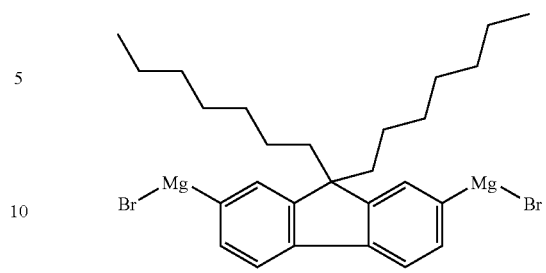

1a) 9,9-diheptyl-2,7-fluoren-ylene-magnesium bromide is produced in this manner, for example, from 9,9-diheptyl-2,7-dibromofluorene and magnesium

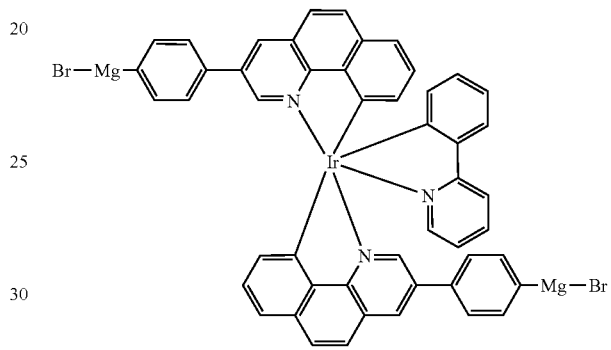

1b) A Grignardized complex of the type $(C^\wedge N)_2$=Ir-(LX) is formed in this manner, for example, using $(C^\wedge N)$=3-(phenyl=4-yl-magnesium bromide)-h-benzoquinoline and LX=phenyl pyridine Alternative Synthesis of the Lithiated Compounds D, E and F 0.1 mol highly purified and dried dibromo-arylene component M (A) or TE (C) and/or the unbrominated arylene component HT (B), dissolved in 300 ml dry ether/toluene 1:1, are provided in an argon atmosphere. While stirring at room temperature, the respective equivalent quantity of butyl lithium is injected through a septum. The syntheses of the required lithiated compounds are complete after 2 hours, and they are immediately used in subsequent reactions.

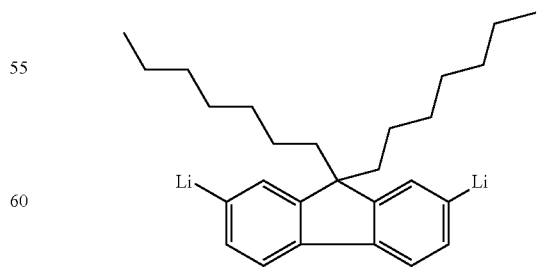

1a) 9,9-diheptyl-2,7-fluoren-ylen-lithium is produced in this manner, for example, from 9,9-diheptyl-2,7-dibromofluorene and butyl lithium

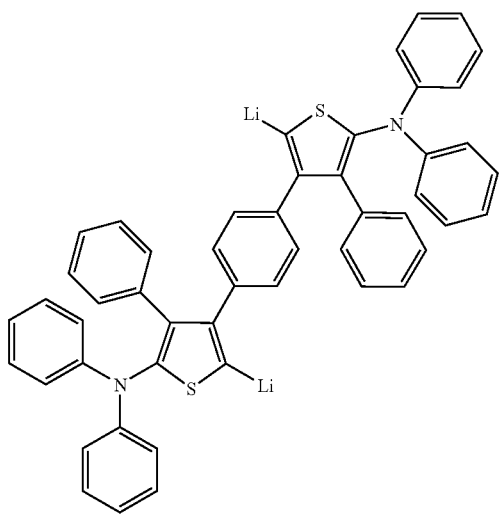

1b) 2,2'-diphenylamino-3,3'-diphenyl-5,5'-dilithio-4,4'-bisthienyl-p-phenylene is produced in this manner, for example, from 2,2'-diphenylamino-3,3'-diphenyl-4,4'-bisthienyl-p-phenylene and butyl lithium

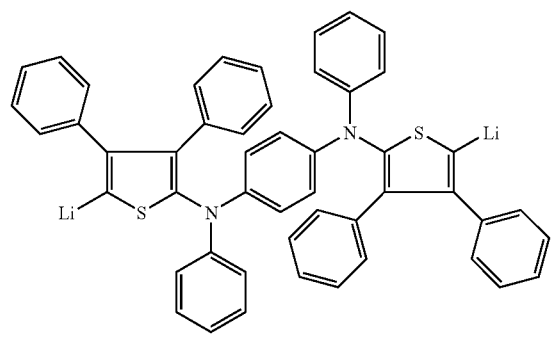

1c) N,N'-diphenyl-N,N'-di-[(3,4-diphenyl-5-yl-lithium)-thien-2yl]-phenylene-1,4-diamine is produced in this manner, for example, from N,N'-diphenyl-N,N'-di-[(3,4-diphenyl)-thien-2-yl]-phenylene-1,4-diamine and butyl lithium

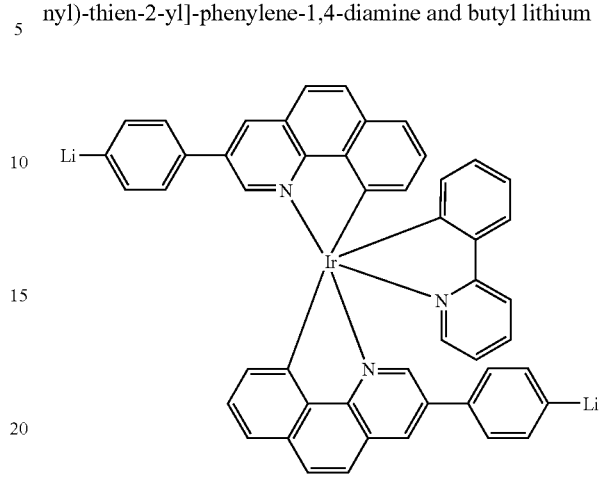

1d) A lithiated complex of the type $(C^{\wedge}N)_2=Ir-(LX)$ is formed in this manner, for example, using $(C^{\wedge}N)=$3-(phenyl-4-yl-lithium)-h-benzoquinoline and LX=phenyl pyridine Synthesis of the Linear Co-polyfluoro-arylene Boranes H The desired parts of the prepared Grignard compounds and/or of the, lithiated compounds (D, E and F), dissolved in THF or ether/toluene 1:1, are transferred under argon and, excluding any moisture, into a bulb that is equipped with a tap funnel, reflux cooler, agitator and argon atmosphere. Boron trifluoride etherate corresponding to the sum of the molar parts of the metallo-organic compounds is injected over the course of 30 minutes through a septum in the reaction bulb and stirred at 60° C. After a reaction time of 2 hours, the co-polyfluoro-arylene borane H that was synthesized in this manner is now available for the next reaction.

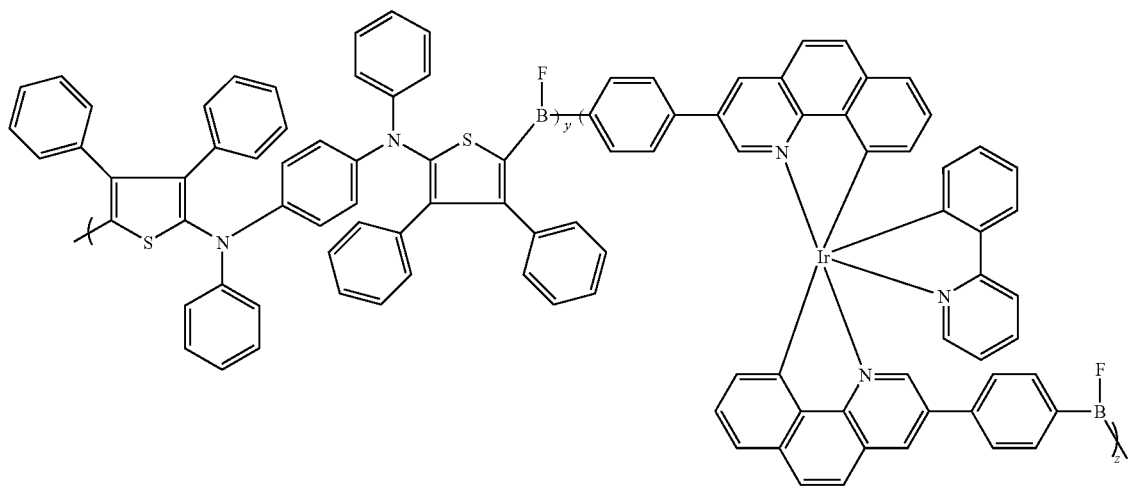

1a) Co-polymeric polyfluoro-arylene borane with 98% HT and 2% TE component is produced in this manner, for example, from the corresponding lithiated HT and TE components (for examples see below) and borotrifluoride etherate.

Synthesis of Grignard Compounds I 0.15 mol freshly etched magnesium shavings are provided in an argon atmosphere in dry ether. While stirring and refluxing, 0.1 mol highly purified and dried arylbromide, dissolved in 150 ml THF, is dropped in, particularly in such a way that the reaction mixture is held at boiling after the start of the reaction. The reaction continues overnight. The Grignard compound I synthesized in this manner should be available after the completion of the co-polyfluoro-arylene borane H.

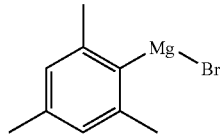

1a) The mesityl-Grignard compound is produced in this manner, for example, from mesityl bromide and magnesium Alternative Synthesis for Lithiated Aryl Compounds I 0.01 mol of highly purified and dried aryl component I, dissolved in 50 ml dry ether/toluene 1:1, is prepared in an argon atmosphere. While stirring at room temperature, the equivalent quantity of butyl lithium is injected through a septum. The synthesis of the needed lithiated compound is complete after 2 hours and is immediately used in subsequent reactions.

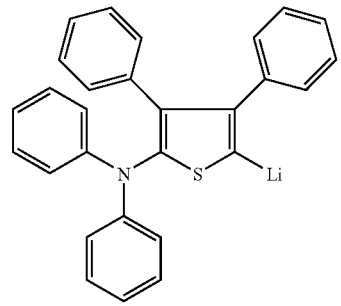

1a) 2-diphenylamino-3,4-diphenyl-thien-5-yl-lithium is produced in this manner, for example, from 2-diphenylamino-3,4-diphenyl-thiophene and butyl lithium Synthesis of Posphorescing Co-polyborane K Starting materials are the apparatus with available co-polyfluoro-arylene borane H and a metallo-organic compound I.

First, the reflux cooler of the apparatus is replaced with a distillation bridge and the THF solvent is distilled off. The tap funnel is simultaneously filled, using approximately the same volume as the reaction mixture, with dry toluene and dropped in as solvent instead of the THF. After the solvent exchange is complete, the desired dissolved Grignard compound I or, in the alternative, a lithiated compound I is slowly dosed into the tap funnel in an argon atmosphere, excluding moisture and at a stoichiometric ratio in relation to the co-polyfluoro-arylene borane H, and dropped in slowly while the toluene is slightly boiling. The solvent (THF or ether) of the metallo-organic compound I, that is being added dropwise, is distilled off at the same time. After separating THF or ether the distillation bridge is exchanged once more with the reflux cooler, and heating continues for another 5 hours with reflux. After cooldown, the reaction mixture is poured over ice/HCl, and the toluene phase is separated. The toluene is completely distilled off at the rotary evaporator; the residue is then dissolved in some THF and precipitated in ethanol while stirring. Further purification of the product is effected by repeated dissolution in THF and repeated precipitation in ethanol.

Example 30:

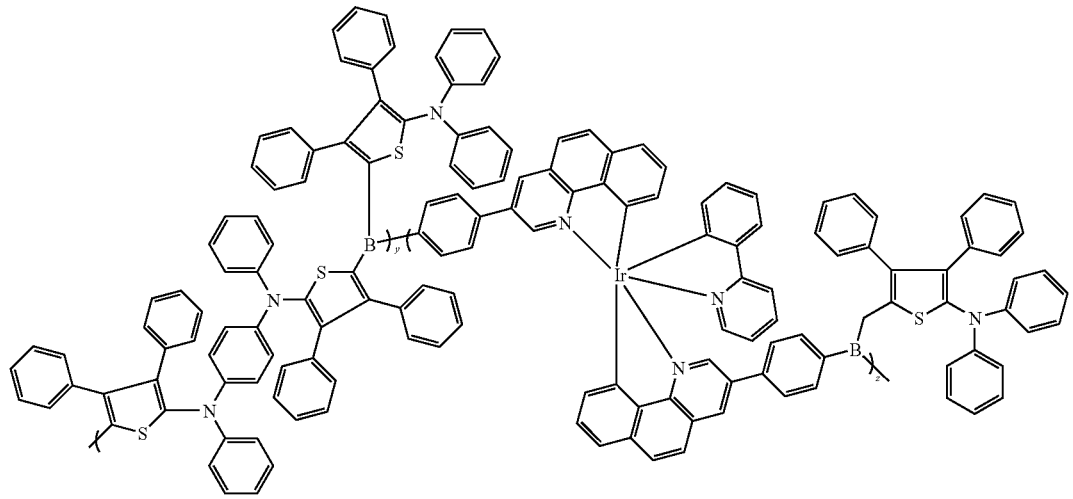

a) An iridium complex containing phosphorescing co-polyborane K with a component ratio of M:HT:TE=0:49:1, temperature limit [Tg]:85° C., $\lambda_{max}$=480 nm, GPC: $M_w$=24500 g/mol is produced in this manner, for example, from co-polyfluoro-arylene borane H (1a) and 2-diphenylamino-3,4-diphenyl-thien-5-yl-lithium I.

OLED Characteristic

Figure 2:
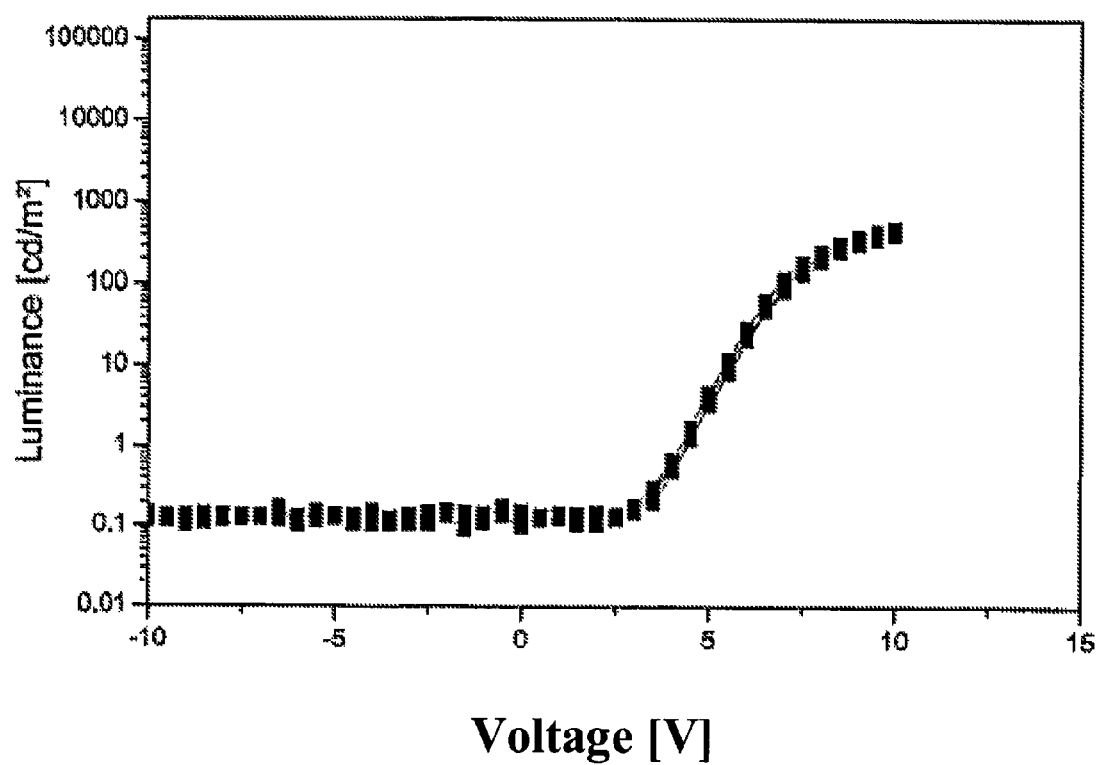
FIG. 2 is a graph of luminance as a function of voltage for an embodiment of an OLED.

An OLED was built using the following order of layers:
Anode: ITO (indium tin oxide)
120 nm Pedot
80 nm emitter (according to the example copolyborane K a)
35 nm Alq3
Cathode 3 nm LiF, 150 nm Al
a) Current density
FIG. 1 shows current density as a function of voltage.
b) Efficiency
FIG. 2 shows luminance as a function of voltage.

The new materials are suitable for the manufacture of electroluminescent diodes in the different colors of the visible spectral range (blue to red). In the same way, these materials can be converted via poly-co-reactions at corresponding ratios to materials that show electroluminescence in the proximity of the white point.

These polymeric materials can be worked-up with all processes that are applied from solution (e.g., spin coating, knife coating, screen printing, ink jet printing).

The materials are, in terms of preparation, accessible in high yields and are derived from triplet-emitting emitters that are incorporated in arylated boranes, and the selection of the arylene fragments (donor/acceptor structure) hereby influences the electronic properties and therewith the color of the respective compound.

To be noted, in particular, is the fact that none of the usual metal-catalysis-based coupling reactions are required to synthesize these polymeric materials (which eliminates the complex separation of the catalyst and the risk of contamination of the polymer with quencher particles) thus constituting a considerable cost reduction of the synthesis because expensive palladium catalysts are not required and need not be separated.

In particular white-emitting materials are of particularly great interest for the production of light sources and full-color displays in which full color is achieved by filtering. The advantage of white-light driven full-color displays is the color-independent aging of the emitting material.

The invention claimed is:
1. A phosphorescent copolyaryl borane of type K,

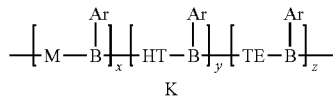

wherein:
x, y and z are molar parts and add up to 1 and the molar parts y and z each are >0,
hydrogen atoms are bonded at the ends,
M, HT and TE each represent a type of arylene component,
M is a matrix structure comprising an arylene structure, the arylene structure being any bivalently linking single- or multi-nucleic aromatic and/or heteroaromatic structure,
HT is a substituted 2-amino-thiophene or 2-amino-thiazole structure with hole-transport capability,
TE is a bivalent, phosphorescent organo-metallic complex of the following structure:

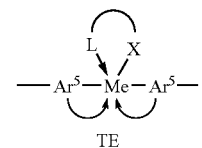

wherein Me denotes a metal of group 8, 9 or 10, $Ar^5$ is an arylene ligand that can form a complex with the metal Me and simultaneously is capable of polymeric linking,
TE does not have the ligand (L-X) if the metal Me is platinum, and for all other Me L-X is a complex-forming ligand, and
Ar is a carbocyclic or heterocyclic aryl moiety of which 0, 1 or more of the hydrogen atoms are each substituted by branched or linear aryl moieties or alkoxy moieties ($C_1$ to $C_{10}$), phenyl moieties or diphenyl or naphthylphenylamino groups.

2. The phosphorescent copolyaryl borane of claim 1, wherein z has a value of between 0.01 and 0.1.

3. The phosphorescent copolyaryl borane of claim 1, wherein the arylene structure M is a 2,7-fluorenylene structure that is unsubstituted, or is substituted in the 9-position with a linear or branched alkyl moiety ($C_1$ to $C_{10}$).

4. The phosphorescent copolyaryl borane of claim 1, wherein the arylene structure M is a radical formed from one of the following groups a1 to x

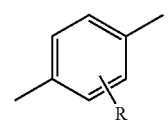

a1

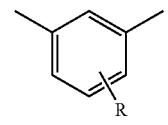

a2

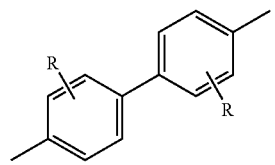

b1

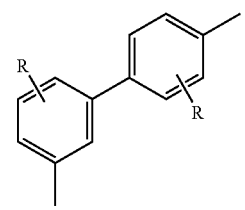

b2

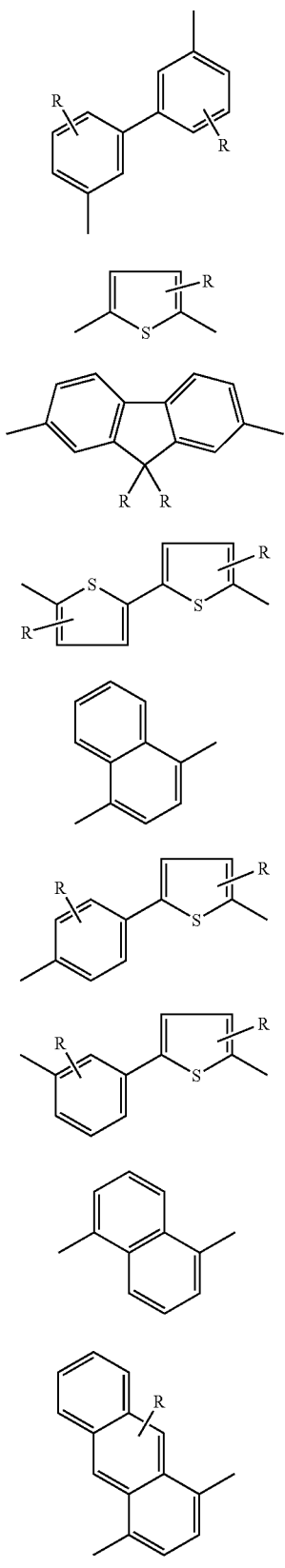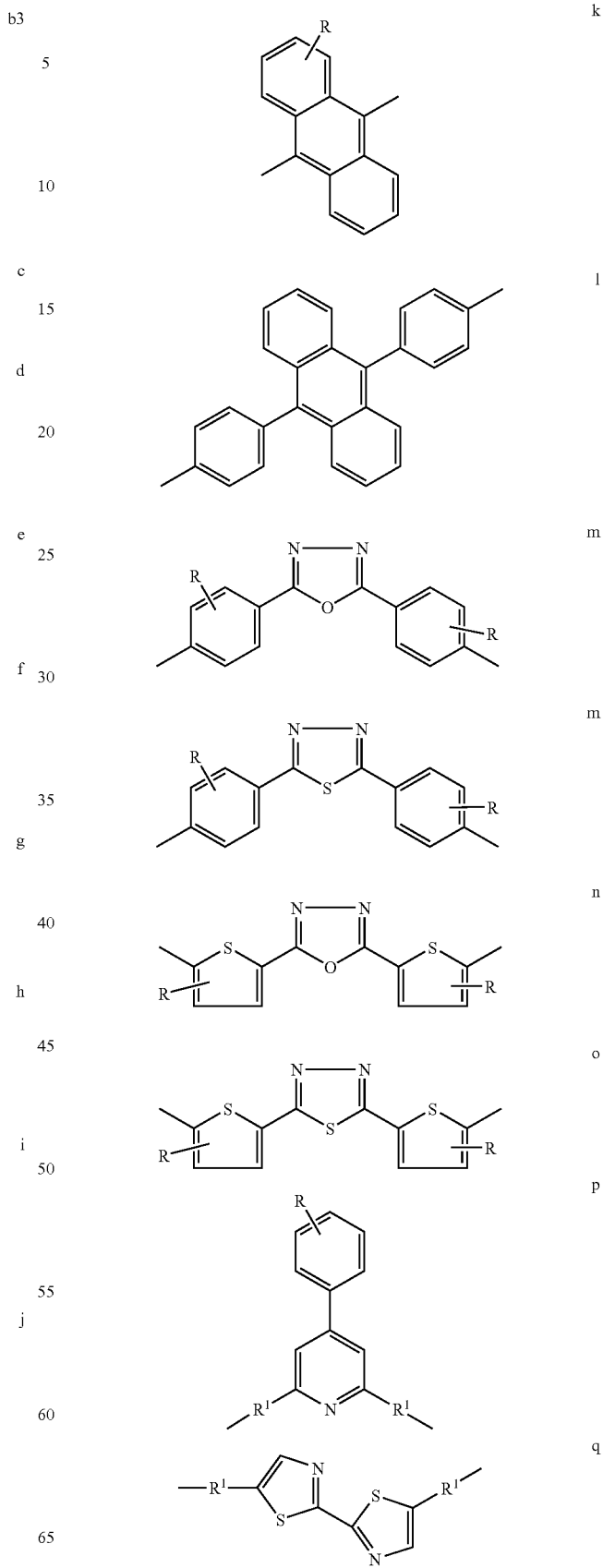

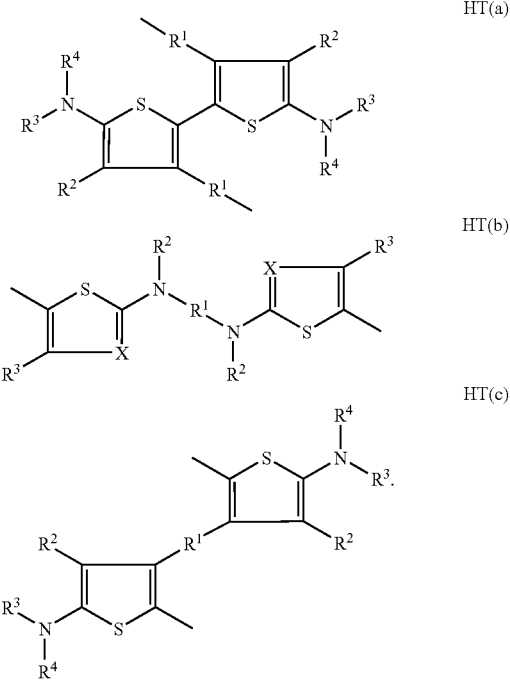

the solubility of which in organic solvents is modifiable by arranging one or more of the linear or branched alkyl substituents or alkoxy substituents R, and also by the alkyl-substituted arylene substituent $R^1$, or by the 2,7-disubstituted 9,9-dialkylfluorenylene structures that are substituted with branched or linear $C_5$ to $C_{10}$ alkyl groups.

5. The phosphorescent copolyaryl borane of claim 4 wherein, the substituted 2-amino-thiophene or 2-amino-thiazole structure HT with hole transport capacity is a structure selected from the group of structures HT(a) to HT(c), wherein
HT(a) is a substituted (2,2'-diamino-5,5'bisthienyl)-4,4'-ylene structure,
HT(b) is a substituted bis-N,N'-(thien-2-yl)- and/or bis-N,N'-(1,3-thiazol-2-yl) diaminoarylene structure, and
HT(c) is a substituted (2,2'-diamino)-bis-(4,4'thienyl)-arylene-5,5'-ylene structure, respectively in accordance with the formulas below,
and the substituents $R^2$, $R^3$ and $R^4$ denote aryl groups Ar that in turn are unsubstituted or substituted by any additional arrangement of one or several linear or branched alkyl substituents or alkoxy substituents R, and the denotations of the substituents R" are identical for the same index n, and those of substituent $R^1$ are identical to the group for arylene structure M;
and for HT(b) X equals N or C-R

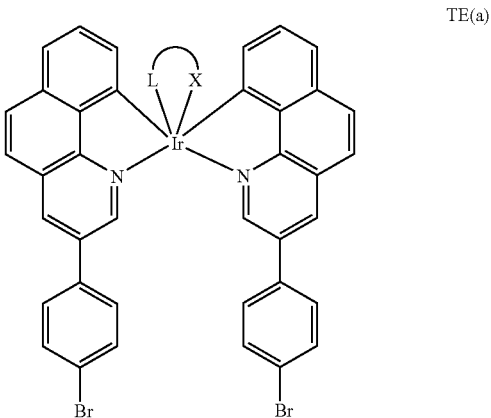

6. The phosphorescent copolyaryl borane of claim 1 wherein the carbocyclic or heterocyclic aryl moiety Ar is a group selected from the group consisting of: mesityl-, phenyl-, biphenylyl-, 1-naphthyl, 2-naphthyl-, 2-diphenyl-, 2-naphthylphenylamino-3,4-diphenyl-thien-5-yl-, 2-diphenyl-, and 2-naphthylphenylamino-3,4-diphenyl-1,3-thiazol-5-yl.

7. The phosphorescent copolyaryl borane of claim 1 wherein the bivalent phosphorescent organo-metallic complex TE has iridium as its central atom Me.

8. The phosphorescent copolyaryl borane of claim 1 wherein the bivalent phosphorescent organo-metallic complex TE is a radical selected from the group consisting of TE(a) to TE(g), TE(a)

-continued
TE(b)
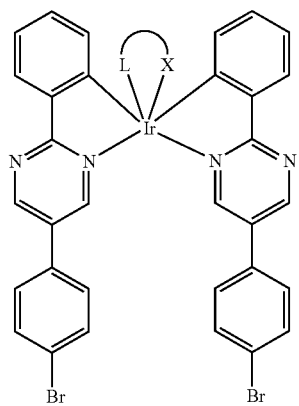
TE(c)
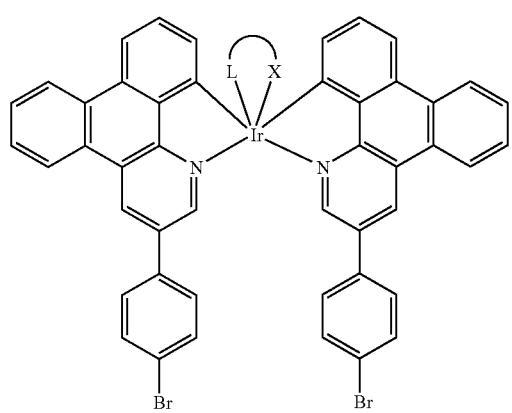
TE(d)
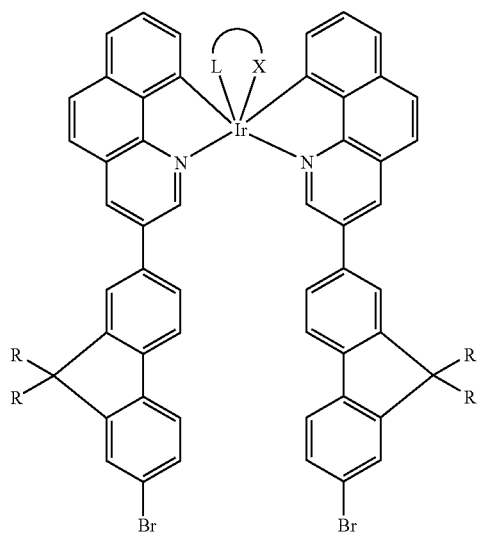
-continued
TE(e)
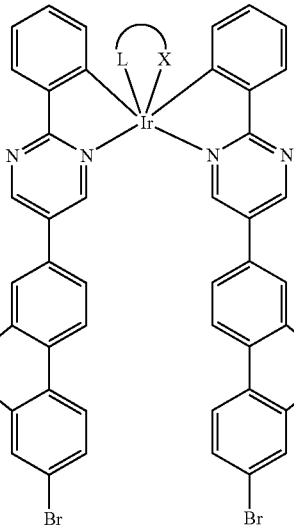
TE(f)
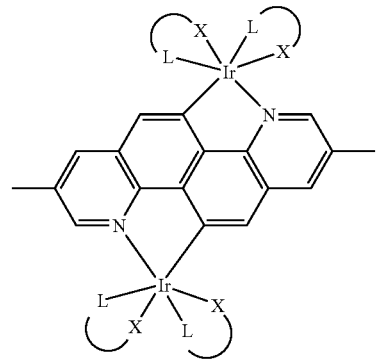
TE(g)
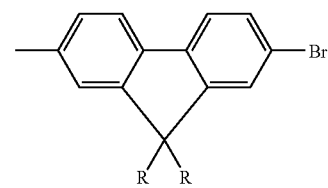

-continued

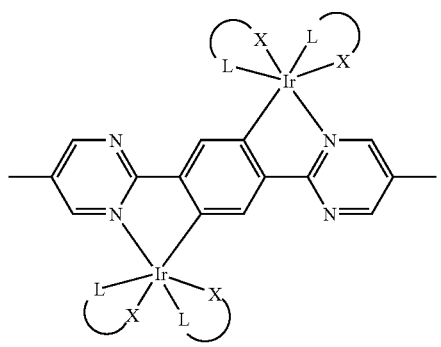

5

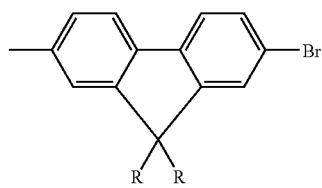

20 and ligand L-X is a ligand selected from the group consisting of complex-forming arylene ligands, 1,3-diketonate ligands, bis-thiazolylmethane or bis-thiazolylamine ligands, picolinate ligands, N-alkylsalicyclaldimino ligands and 8-hydroxyquinolate ligands.

9. The phosphorescent copolyaryl borane of claim 8, wherein the ligand L-X is a ligand selected from the group consisting of a1, a2, a3, a4, a5, a6, a7, b1, b2, c1, c2, c3, c4, d, e and f

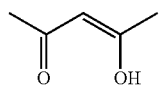 b1

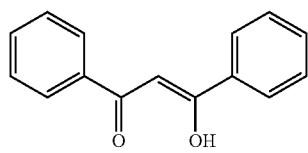 b2

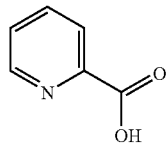 d

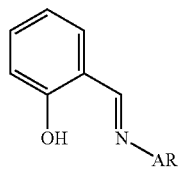 e

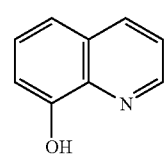 f

-continued

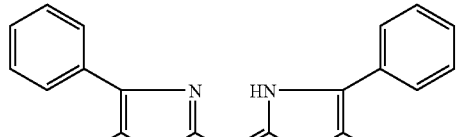 c1

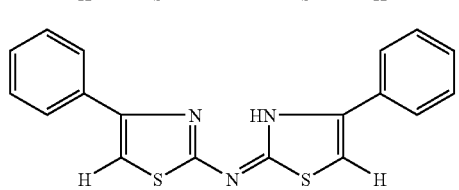 c2

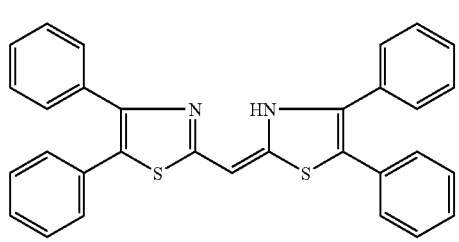 c3

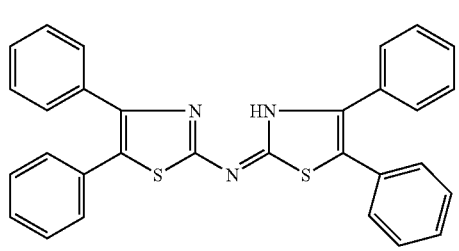 c4

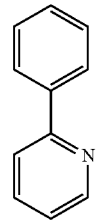 a1

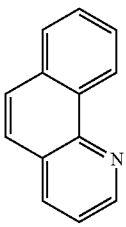 a2

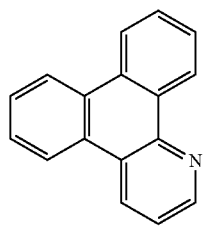 a3

-continued a4
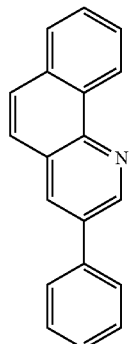

a5
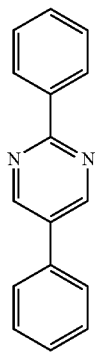

a6
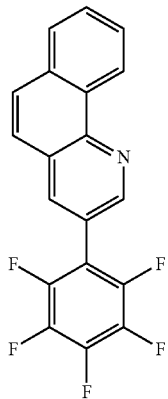

a7
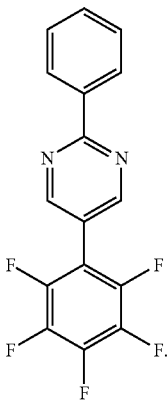

10. An organic light emitting diode, comprising copolyaryl borane of type K of claim 1, wherein the copolyaryl borane is in a triplet-emitting and/or electron-transporting layer of the diode.

11. The phosphorescent copolyaryl borane of claim 1, wherein Me is iridium, ruthenium, osmium or platinum.

12. A method for producing a phosphorescent copolyaryl borane of type K

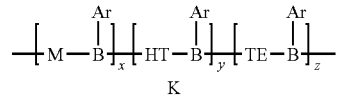

K wherein x, y and z are molar parts and add up to 1 and the molar parts y and z each are >0, hydrogen atoms are bonded at the ends, M, HT and TE each represent a type of arylene component, M is a matrix structure comprising an arylene structure, the arylene structure being any bivalently linking single- or multi-nucleic aromatic and/or heteroaromatic structure, HT is a substituted 2-amino-thiophene or 2-amino-thiazole structure with hole-transport capability, TE is a bivalent, phosphorescent organo-metallic complex of the following structure:

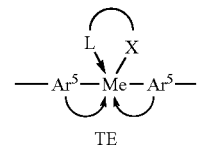

TE wherein Me denotes a metal of group 8, 9 or 10, $Ar^5$ is an arylene ligand that can form a complex with the metal Me and simultaneously is capable of polymeric linking, TE does not have the ligand (L-X) if the metal Me is platinum, and for all other Me L-X is a complex-forming ligand, and Ar is a carbocyclic or heterocyclic aryl moiety of which 0, 1 or more of the hydrogen atoms are each substituted by branched or linear aryl moieties or alkoxy moieties ($C_1$ to $C_{10}$), phenyl moieties or diphenyl or naphthylphenyl-amino groups in accordance with the general synthesis scheme:

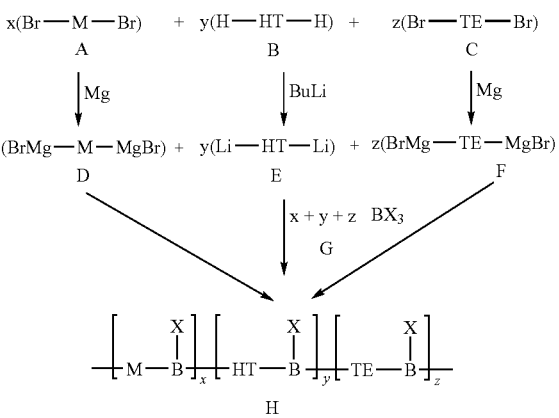

-continued

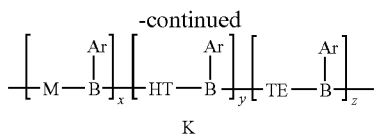

wherein the starting point is the bromo-substituted arylene component M, the hole transport component HT and the bromo-substituted phosphorescent organo-metallic complex TE, the method comprising:

reversing the polarity of the component M, the component HT and the complex TE, either by way of a Grignard reaction or by lithiation to produce a magnesium halide compound or a lithiated compound;

after the reversing, substituting the magnesium or lithium of the magnesium halide compound or the lithiated compound with boron using a boron trihalide to form products H; and in the products H of the substituting, substituting the halogens X on the boron with organic moieties Ar via a Grignard reagent or via a corresponding lithiated reagent.

13. A mixture of at least two different phosphorescing polyaryl boranes of type K, wherein in each individual component polymer two of the aspect ratio variables x, y or z have the value zero, wherein K has the following structure:

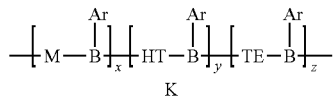

wherein:
hydrogen atoms are bonded at the ends,
M, HT and TE each represent a type of arylene component,
M is a matrix structure comprising an arylene structure, the arylene structure being any bivalently linking single- or multi-nucleic aromatic and/or heteroaromatic structure,
HT is a substituted 2-amino-thiophene or 2-amino-thiazole structure with hole-transport capability,
TE is a bivalent, phosphorescent organo-metallic complex of the following structure:

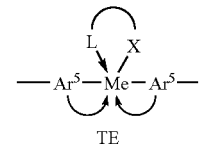

TE wherein Me denotes a metal of group 8, 9 or 10, $Ar^5$ is an arylene ligand that can form a complex with the metal Me and simultaneously is capable of polymeric linking, TE does not have the ligand (L-X) if the metal Me is platinum, and for all other Me L-X is a complex-forming ligand, and Ar is a carbocyclic or heterocyclic aryl moiety of which 0, 1 or more of the hydrogen atoms are each substituted by branched or linear aryl moieties or alkoxy moieties (C1 to C10), phenyl moieties or diphenyl or naphthylphenyl-amino groups wherein the mixture is one of:

a homopolymer containing M and a homopolymer containing HT;

a homopolymer contaning HT and a homopolymer containing TE;

a homopolymer containing M and a homopolymer containing TE; or a homopolymer containing M, a homopolymer containing HT and a homopolymer containing TE.

* * * * *

UNITED STATES PATENT AND TRADEMARK OFFICE
CERTIFICATE OF CORRECTION

PATENT NO. : 7,858,724 B2
APPLICATION NO. : 10/585182
DATED : December 28, 2010
INVENTOR(S) : Kanitz et al.

It is certified that error appears in the above-identified patent and that said Letters Patent is hereby corrected as shown below:

Col. 37, Line 29
In Claim 8, delete "N-alkylsalicyclaldimino" and insert -- N-alkylsalicylaldimino --, therefor.

Col. 40 Line 44
In Claim 12, delete "($C_1$to $C_{10}$)," and insert -- ($C_1$ to $C_{10}$), -- therefor.

Col. 42, Line 25
In Claim 13, delete "(C1 to C10)," and insert -- ($C_1$ to $C_{10}$), -- therefor.

Col 42, Line 30
In Claim 13, delete "containg" and insert -- containing --, therefor.

In Claim 1, Col. 32, lines 25-35 (approx.) should read,

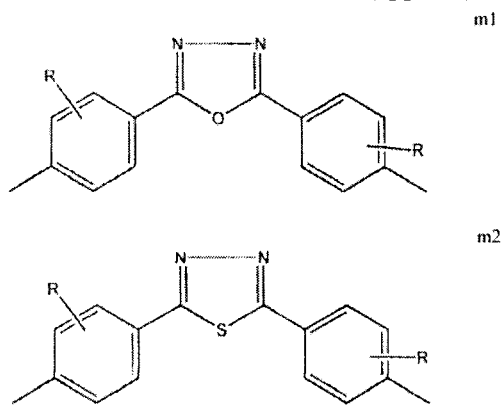

Signed and Sealed this
Twenty-ninth Day of November, 2011

David J. Kappos
*Director of the United States Patent and Trademark Office*

CERTIFICATE OF CORRECTION (continued)
U.S. Pat. No. 7,858,724 B2

In Claim 4, Col 33, lines 25-30 (approx.) should read,

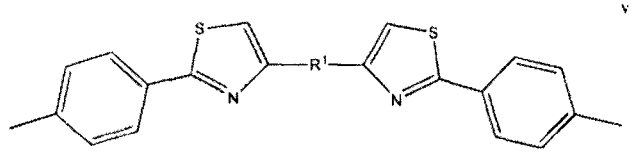

In Claim 2, Col. 36, lines 25-55 (approx.) should read,

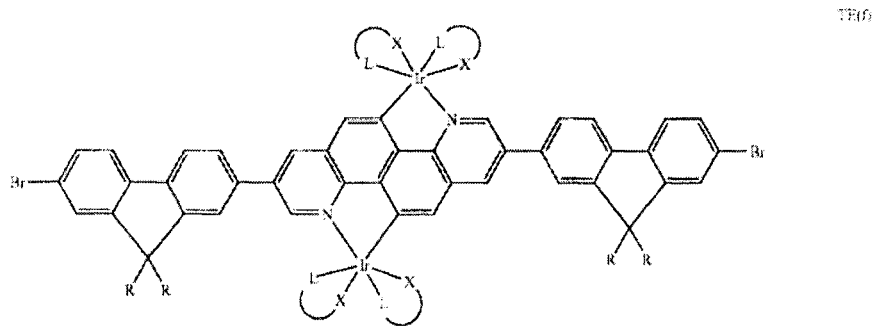

In Claim 8, Col. 36, line 60- Col. 37, line 25 (approx.) should read,

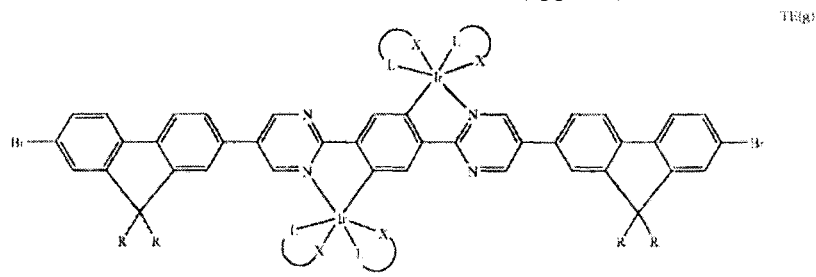

In Claim 2, Col. 37, lines 55-60 (approx.) should read,

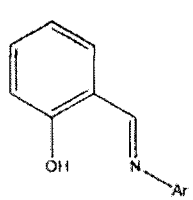

CERTIFICATE OF CORRECTION (continued)
U.S. Pat. No. 7,858,724 B2

In Col. 4, lines 15-35 (approx.) should read,

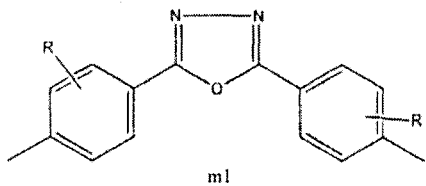

m1

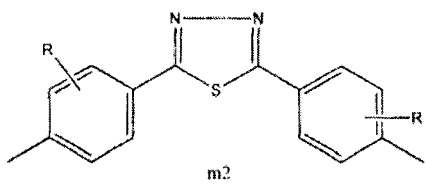

m2

UNITED STATES PATENT AND TRADEMARK OFFICE
CERTIFICATE OF CORRECTION

PATENT NO. : 7,858,724 B2  
APPLICATION NO. : 10/585182  
DATED : December 28, 2010  
INVENTOR(S) : Kanitz et al.

Page 1 of 2

It is certified that error appears in the above-identified patent and that said Letters Patent is hereby corrected as shown below:

In Col. 4, Lines 15-35 (approx.) should read,

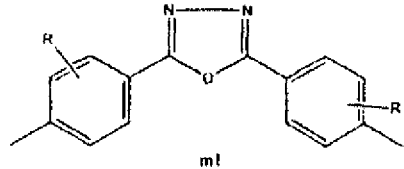

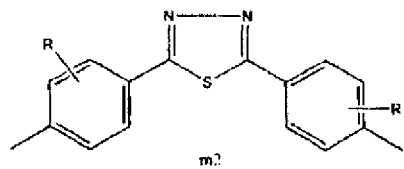

In Claim 4, Col. 32, Lines 25-35 (approx.) should read,

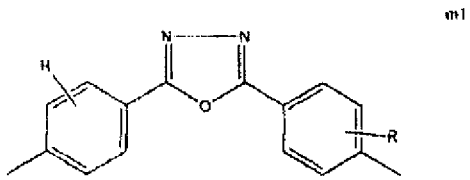

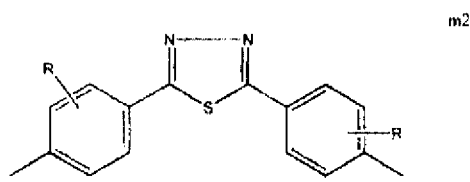

This certificate supersedes the Certificate of Correction issued November 29, 2011.

Signed and Sealed this  
Thirtieth Day of October, 2012

David J. Kappos  
*Director of the United States Patent and Trademark Office*

CERTIFICATE OF CORRECTION (continued)
U.S. Pat. No. 7,858,724 B2

In Claim 4, Col. 33, Lines 25-30 (approx.) should read,

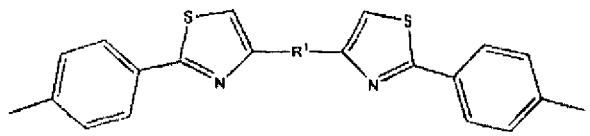

In Claim 8, Col. 36, Lines 25-55 (approx.) should read,

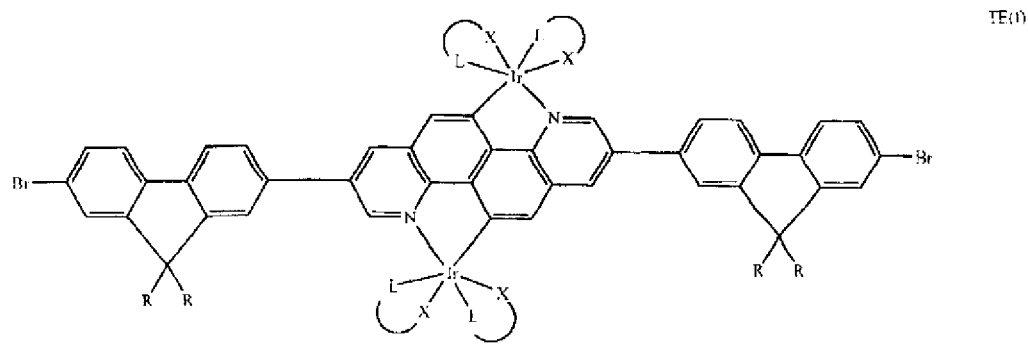

In Claim 8, Col. 36, Line 60- Col. 37, line 25 (approx.) should read,

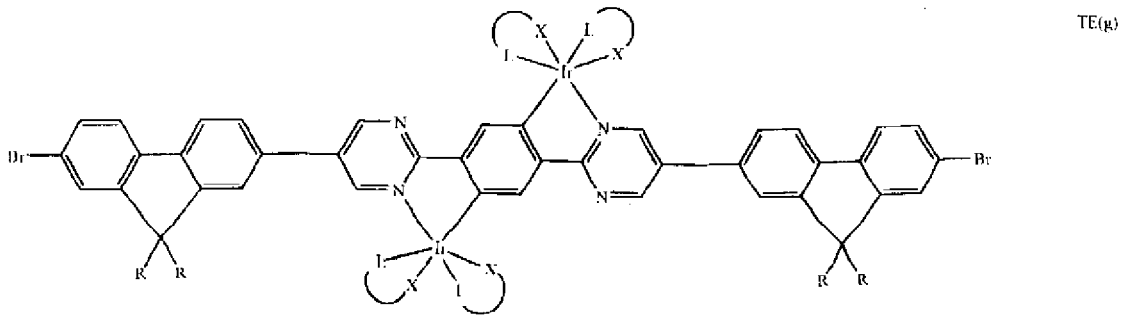

In Claim 8, Col. 37, Line 29, delete "N-alkylsalicyclaldimino" and insert -- N-alkylsalicylaldimino --, therefor.

In Claim 9, Col. 37, Lines 55-60 (approx.) should read,

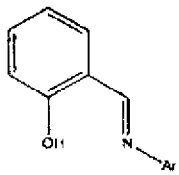

In Claim 12, Col. 40, Line 44, delete "($C_1$to $C_{10}$)," and insert -- ($C_1$ to $C_{10}$), -- therefor.

In Claim 13, Col. 42, Line 23-24, delete "(C1 to C10)," and insert -- ($C_1$ to $C_{10}$), -- therefor.

In Claim 13, Col. 42, Line 30, delete "containg" and insert -- containing --, therefor.